United States Patent [19]

Huang et al.

[11] Patent Number: 5,418,254

[45] Date of Patent: May 23, 1995

[54] SUBSTITUTED CYCLOPENTADIENYL COMPOUNDS FOR THE TREATMENT OF INFLAMMATION

[75] Inventors: Horng-Chih Huang; David R. Reitz, both of Chesterfield, Mo.

[73] Assignee: G. D. Searle & Co., Skokie, Ill.

[21] Appl. No.: 238,101

[22] Filed: May 4, 1994

[51] Int. Cl.$^6$ .............................................. A61K 31/18
[52] U.S. Cl. .................................. 514/604; 514/344; 514/345; 514/709; 560/102; 562/492; 568/34; 568/33; 564/84; 549/345; 549/346; 549/286; 549/290; 549/340; 549/342
[58] Field of Search ............... 514/344, 345, 604, 709; 560/102; 562/492; 568/34, 33; 564/84; 549/345, 346, 286, 290, 340, 342

[56] References Cited

U.S. PATENT DOCUMENTS 4,946,993  8/1990  Cortes .

OTHER PUBLICATIONS

T. Hla and K. Neilson, *Proc. Natl. Acad. Sci. USA, 89,* 7384-7388 (Mar. 1992).
J. L. Masferrer et al. *Proc. Natl. Acad. Sci. USA, 89,* 3917 (Feb. 1992).
E. Meade et al., *J. Biol. Chem., 268,* 6610 (Jun. 1993).
N. Futaki et al, *Prostaglandins, 47,* 1 (Nov. 1994).
C. Allen et al, *J. Org. Chem., 11,* 268 (Jul. 1946).
H. Zimmerman and J. Pincock, *J. Amer. Chem. Soc., 95,* 3246 (1973).
K. Hirao et al, *J. Chem. Soc., Chem. Commun.,* 300 (Sep. 1984).

*Primary Examiner*—James H. Reamer
*Attorney, Agent, or Firm*—Joseph W. Bulock

[57] ABSTRACT

A class of 2,3-substituted cyclopenta-2,4-dienyl compounds is described for use in treating inflammation and inflammation-related disorders. Compounds of particular interest are defined by Formula II:

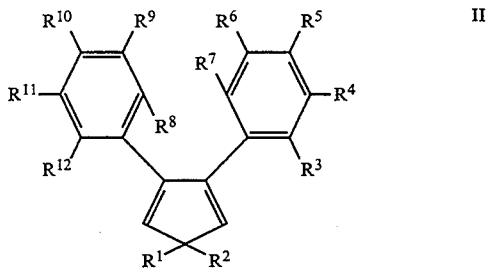

wherein each of $R^1$ and $R^2$ is independently selected from hydrido, lower alkyl, lower hydroxyalkyl, halo, lower haloalkyl, lower alkoxycarbonyl and carboxyl; and wherein each of $R^3$ through $R^{12}$ is independently selected from hydrido, halo, lower alkyl, lower alkylthio, cyano, hydroxyl, mercapto, lower haloalkyl, lower haloalkoxy, lower alkoxy, lower hydroxyalkyl, lower alkoxyalkyl, lower alkylsulfonyl, lower haloalkylsulfonyl and sulfamyl; provided $R^5$ and $R^{10}$ are not both hydrido or methoxy; or a pharmaceutically suitable salt or prodrug thereof.

38 Claims, No Drawings

SUBSTITUTED CYCLOPENTADIENYL COMPOUNDS FOR THE TREATMENT OF INFLAMMATION

FIELD OF THE INVENTION

This invention is in the field of antiinflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). Recently, the sequence of another heretofore unknown enzyme in the human arachidonic acid/prostaglandin pathway has been reported by T. Hla and K. Nielson, Proc. Natl. Acad. Sci, USA, 89, 7384 (1992) and named "cyclooxygenase II (COX II)" or "prostaglandin G/H synthase II". The discovery of an inducible enzyme associated with inflammation provides a viable target of inhibition which more effectively reduces inflammation and produces fewer and less drastic side effects. Cyclooxygenase II is inducible by cytokines or endotoxins and such induction is inhibited by glucocortoids (J. Masferrer, et al, Proc. Natl. Acad. Sci, USA, 89, 3917 (1992)). The 6-methoxy-2-napthylacetic acid metabolite of nabumetone has been found by E. Meade et al to selectively inhibit the COX II enzyme (J. Biol. Chem., 268, 6610 (1993)). In addition, Futaki et al (Prostaglandins, 47, 1 (1994)) have reported that N-(2-cyclohexyloxy-4-nitrophenyl)methanesulfonamide inhibits the COX II enzyme.

The substituted cyclopenta-2,4-dienyl compounds disclosed herein selectively inhibit cyclooxygenase II over cyclooxygenase I and relieve the effects of inflammation. These compounds, in addition, do not display substantial inhibition of cyclooxygenase I and produce a reduced amount of side effects.

Diarylcyclopentenes are described in a copending application, serial number 08/146,359.

U.S. Pat. No. 4,946,993 to Cortes, describes the use of aryl substituted cyclopentadienes to form N-phosphonomethylglycine.

Allen et al [J. Org. Chem., 11, 268 (1946)] describe the formation of 3,4-diphenylcyclopentadiene.

Zimmerman and Pinock [J. Amer. Chem. Soc., 95, 3246 (1973)] describe the synthesis of 5,5-dimethyl-2,3-diphenylcyclopentadiene from diacetylenic compounds.

Hirao et al [J. Chem. Soc., Chem. Commun., 300 (1984)] describe the synthesis of norbornadienes from substituted cyclopentadienes and acetylenes. Specifically, 1,1'-(4,4-dimethyl-2,5-cyclopentadien-1,2-diyl)-bis[4-methoxybenzene is described.

DESCRIPTION OF THE INVENTION

A class of substituted cyclopenta-2,4-diene compounds useful in treating inflammation-related disorders is defined by Formula I:

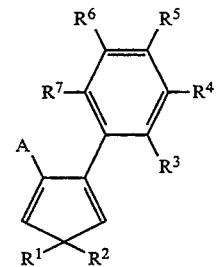

wherein A is selected from

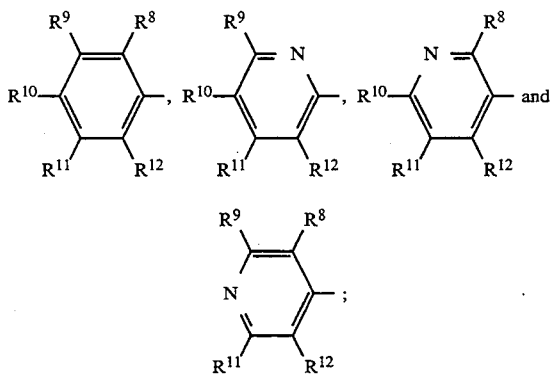

wherein each of $R^1$ and $R^2$ is independently selected from alkyl, hydrido, hydroxyalkyl, halo, haloalkyl, alkoxycarbonyl and carboxyl; and wherein each of $R^3$ through $R^{12}$ is independently selected from hydrido, halo, alkyl, alkylthio, cyano, hydroxyl, mercapto, haloalkyl, alkoxy, haloalkoxy, hydroxyalkyl, alkoxyalkyl, alkylsulfonyl, haloalkylsulfonyl and sulfamyl;

provided that when A is

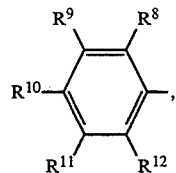

$R^5$ and $R^{10}$ are not both hydrido or methoxy; or a pharmaceutically suitable salt thereof.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, osteoarthritis, systemic lupus erythematosus and juvenile arthritis. Such compounds of Formula I would be useful in the treatment of asthma, bronchitis, menstrual cramps, tendinitis, bursiris, and skin related conditions such as psoriasis, eczema, burns and dermatitis. Compounds of Formula I also would be useful to treat gastrointestinal conditions such as inflammatory bowel syndrome, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroidiris, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as anti-inflammatory agents, such as for the treatment of arthritis, with the additional benefit of having significantly less harmful side effects.

Preferably, the compounds have a cyclooxygenase II $IC_{50}$ less than about 0.1 $\mu M$, and also have a selectivity ratio of cyclooxygenase II inhibition over cyclooxygenase I inhibition of at least 50, and more preferably of at least 100. Even more preferably, the compounds have a cyclooxygenase I $IC_{50}$ of greater than about 0.5 $\mu M$, and more preferably of greater than 5 $\mu M$. Such preferred selectivity may indicate an ability to reduce the incidence of common NSAID-induced side effects, such as ulcers.

A preferred class of compounds consists of those compounds of Formula I wherein each of $R^1$ and $R^2$ is independently selected from hydrido, lower alkyl, lower hydroxyalkyl, halo, lower haloalkyl, lower alkoxycarbonyl and carboxyl; and wherein each of $R^3$ through $R^{12}$ is independently selected from hydrido, halo, lower alkyl, lower alkylthio, cyano, hydroxyl, mercapto, lower haloalkyl, lower haloalkoxy, lower alkoxy, lower hydroxyalkyl, lower alkoxyalkyl, lower alkylsulfonyl, lower haloalkylsulfonyl and sulfamyl.

A class of compounds of particular interest consists of those compounds of Formula I wherein each of $R^1$ and $R^2$ is independently selected from hydrido, methyl, ethyl, propyl, butyl, pentyl, isopropyl, isobutyl, tertbutyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, hydroxyl, mercapto, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tertbutoxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, trifluoromethylsulfonyl and sulfamyl.

Within Formula I there is a subclass of compounds of high interest represented by Formula II:

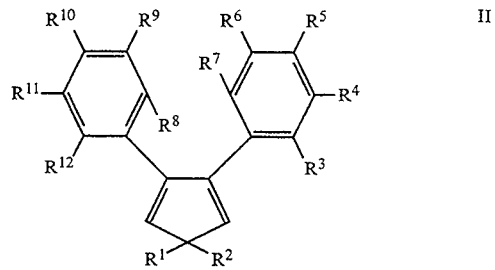

wherein each of $R^1$ and $R^2$ is independently selected from alkyl, hydrido, hydroxyalkyl, halo, haloalkyl, alkoxycarbonyl and carboxyl; and wherein each of $R^3$ through $R^{12}$ is independently selected from hydrido, halo, alkyl, alkylthio, cyano, hydroxyl, mercapto, haloalkyl, alkoxy, haloalkoxy, hydroxyalkyl, alkoxyalkyl, alkylsulfonyl, haloalkylsulfonyl and sulfamyl; provided $R^5$ and $R^{10}$ are not both hydrido or methoxy.

A preferred class of compounds consists of those compounds of Formula II wherein each of $R^1$ and $R^2$ is independently selected from hydrido, lower alkyl, lower hydroxyalkyl, halo, lower haloalkyl, lower alkoxycarbonyl and carboxyl; and wherein each of $R^3$ through $R^{12}$ is independently selected from hydrido, halo, lower alkyl, lower alkylthio, cyano, hydroxyl, mercapto, lower haloalkyl, lower haloalkoxy, lower alkoxy, lower hydroxyalkyl, lower alkoxyalkyl, lower alkylsulfonyl, lower haloalkylsulfonyl and sulfamyl.

A class of compounds of particular interest consists of those compounds of Formula II wherein each of $R^1$ and $R^2$ is independently selected from hydrido, methyl, ethyl, propyl, butyl, pentyl, isopropyl, isobutyl, tertbutyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, hydroxyl, mercapto, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tertbutoxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, trifluoromethylsulfonyl and sulfamyl.

A family of specific compounds of particular interest within Formula II consists of compounds and pharmaceutically-acceptable salts thereof as follows:

1-methylsulfonyl-4-[4-phenylcyclopenta-2,4-dien-3-yl]benzene;
1-methylsulfonyl-4-[4-(4-fluorophenyl)cyclopenta-2,4-dien-3-yl]benzene;
1-methylsulfonyl-4-[4-(4-chlorophenyl)cyclopenta-2,4-dien-3-yl]benzene
1-methylsulfonyl-4-[4-(4-bromophenyl)cyclopenta-2,4-dien-3-yl]benzene
1-methylsulfonyl-4-[4-(4-iodophenyl)cyclopenta-2,4-dien-3-yl]benzene
1-methylsulfonyl-4-[4-(4-methylphenyl)cyclopenta-2,4-dien-3-yl]benzene
1-methylsulfonyl-4-[4-(4-ethylphenyl)cyclopenta-2,4-dien-3-yl]benzene
1-methylsulfonyl-4-[4-(4-methoxyphenyl)cyclopenta-2,4-dien-3-yl]benzene;
1-methylsulfonyl-4-[4-(4-methylthiophenyl)cyclopenta-2,4-dien-3-yl]benzene;
1-methylsulfonyl-4-[4-(4-cyanophenyl)cyclopenta-2,4-dien-3-yl]benzene;
1-methylsulfonyl-4-[4-(4-trifluoromethylphenyl) cyclopenta-2,4-dien-3-yl]benzene;
1-methylsulfonyl-4-[4-(4-hydroxymethylphenyl) cyclopenta-2,4-dien-3-yl]benzene;
1-methylsulfonyl-4-[4-(4-methoxymethylphenyl) cyclopenta-2,4-dien-3-yl]benzene;
1-methylsulfonyl-4-[4-(3-methyl-4-methoxyphenyl) cyclopenta-2,4-dien-3-yl]benzene;
1-methylsulfonyl-4-[4-(3,4-dimethylphenyl) cyclopenta-2,4-alien-3-yl]benzene;
1-methylsulfonyl-4-[4-(3-methyl-4-fluorophenyl) cyclopenta-2,4-dien-3-yl]benzene;
1-methylsulfonyl-4-[4-(3-methyl-4-chlorophenyl) cyclopenta-2,4-dien-3-yl]benzene;
1-methylsulfonyl-4-[4-(3-methyl-4-trifluoromethylphenyl) cyclopenta-2,4-dien-3-yl]benzene;
1-methylsulfonyl-4-[4-(3-fluoro-4-methoxyphenyl) cyclopenta-2,4-dien-3-yl]benzene;
1-methylsulfonyl-4-[4-(3-fluoro-4-methylphenyl) cyclopenta-2,4-dien-3-yl]benzene;
1-methylsulfonyl-4-[4-(3,4-difluorophenyl) cyclopenta-2,4-dien-3-yl]benzene;
1-methylsulfonyl-4-[4-(3-fluoro-4-chlorophenyl) cyclopenta-2,4-dien-3-yl]benzene;
1-methylsulfonyl-4-[4-(3-fluoro-4-trifluoromethylphenyl) cyclopenta-2,4-dien-3-yl]benzene;
1-methylsulfonyl-4-[4-(3-chloro-4-methoxyphenyl) cyclopenta-2,4-dien-3-yl]benzene;
1-methylsulfonyl-4-[4-(3-chloro-4-methylphenyl) cyclopenta-2,4-dien-3-yl]benzene;
1-methylsulfonyl-4-[4-(3-chloro-4-fluorophenyl) cyclopenta-2,4-dien-3-yl]benzene;
1-methylsulfonyl-4-[4-(3,4-dichlorophenyl) cyclopenta-2,4-dien-3-yl]benzene;
1-methylsulfonyl-4-[4-(3-chloro-4-trifluoromethylphenyl) cyclopenta-2,4-dien-3-yl]benzene;
1-methylsulfonyl-4-[4-(3-trifluoromethyl-4-methoxyphenyl) cyclopenta-2,4-dien-3-yl]benzene;
1-methylsulfonyl-4-[4-(3-trifluoromethyl-4-methylphenyl) cyclopenta-2,4-dien-3-yl]benzene;
1-methylsulfonyl-4-[4-(3-triftuoromethyl-4-fluorophenyl) cyclopenta-2,4-dien-3-yl]benzene;
1-methylsulfonyl-4-[4-(3-trifluoromethyl-4-chlorophenyl) cyclopenta-2,4-dien-3-yl]benzene;
1-methylsulfonyl-4-[4-(3,4-bis(trifluoromethyl)phenyl) cyclopenta-2,4-dien-3-yl]benzene;
4-[4-phenylcyclopenta-2,4-dien-3-yl]benzenesulfonamide;
4-[4-(4-fluorophenyl)cyclopenta-2,4-dien-3-yl]benzenesulfonamide;
4-[4-(4-chlorophenyl)cyclopenta-2,4-dien-3-yl]benzenesulfonamide;
4-[4-(4-bromophenyl)cyclopenta-2,4-dien-3-yl]benzenesulfonamide;
4-[4-(4-iodophenyl)cyclopenta-2,4-dien-3-yl]benzenesulfonamide;
4-[4-(4-methylphenyl)cyclopenta-2,4-dien-3-yl]benzenesulfonamide;
4-[4-(4-ethylphenyl)cyclopenta-2,4-dien-3-yl]benzenesulfonamide;
4-[4-(4-methoxyphenyl)cyclopenta-2,4-dien-3-yl]benzenesulfonamide;
4-[4-(4-methylthiophenyl)cyclopenta-2,4-dien-3-yl]benzenesulfonamide;
4-[4-(4-cyanophenyl)cyclopenta-2,4-alien-3-yl]benzenesulfonamide;
4-[4-(4-trifluoromethylphenyl)cyclopenta-2,4-dien-3-yl]benzenesulfonamide;
4-[4-(4-hydroxymethylphenyl)cyclopenta-2,4-dien-3-yl]benzenesulfonamide;
4-[4-(4-methoxymethylphenyl)cyclopenta-2,4-dien-3-yl]benzenesulfonamide;
4-[4-(3-methyl-4-methoxyphenyl)cyclopenta-2,4-dien-3-yl]benzenesulfonamide;
4-[4-(3,4-dimethylphenyl)cyclopenta-2,4-dien-3-yl]benzenesulfonamide;
4-[4-(3-methyl-4-fluorophenyl)cyclopenta-2,4-dien-3-yl]benzenesulfonamide;
4-[4-(3-methyl-4-chlorophenyl)cyclopenta-2,4-dien-3-yl]benzenesulfonamide;
4-[4-(3-methyl -4- trifluoromethylphenyl)cyclopenta-2,4-dien-3-yl]benzenesulfonamide;
4-[4-(3-fluoro -4-methoxyphenyl)cyclopenta-2,4-dien-3-yl]benzenesulfonamide;
4-[4-(3-fluoro-4-methylphenyl)cyclopenta-2,4-dien-3-yl]benzenesulfonamide;
4-[4-(3,4-difluorophenyl)cyctopenta-2,4-alien-3-yl]benzenesulfonamide;
4-[4-(3-fluoro-4-chlorophenyl)cyclopenta-2,4-dien-3-yl]benzenesulfonamide;
4-[4-(3-fluoro-4-trifluoromethylphenyl)cyclopenta-2,4-dien-3-yl]benzenesulfonamide;
4-[4-(3-chloro-4-methoxyphenyl)cyclopenta-2,4-dien-3-yl]benzenesulfonamide;
4-[4-(3-chloro-4-methylphenyl)cyclopenta-2,4-dien-3-yl]benzenesulfonamide;
4-[4-(3-chloro-4-fluorophenyl)cyclopenta-2,4-dien-3-yl]benzenesulfonamide;
4-[4-(3,4-dichlorophenyl)cyclopenta-2,4-dien-3-yl]benzenesulfonamide;
4-[4-(3-chloro-4-trifluoromethylphenyl)cyclopenta-2,4-dien-3-yl]benzenesulfonamide;
4-[4-(3-trifluoromethyl-4-methoxyphenyl)cyclopenta-2,4-dien-3-yl]benzenesulfonamide;
4-[4-(3-trifluoromethyl-4-methylphenyl)cyclopenta-2,4-dien-3-yl]benzenesulfonamide;
4-[4-(3-trifluoromethyl-4-fluorophenyl)cyclopenta-2,4-dien-3-yl]benzenesulfonamide;
4-[4-(3-trifluoromethyl-4-chlorophenyl)cyclopenta-2,4-dien-3-yl]benzenesulfonamide;
4-[4-(3,4-bis(trifluoromethyl)phenyl)cyclopenta-2,4-dien-3-yl]benzenesulfonamide;
1-methylsulfonyl-4-[4-(4-fluorophenyl)-1,1-dimethylcyclopenta-2,4-dien-3-yl]benzene;
1-methylsulfonyl-4-[4-(4-fluorophenyl)-1,1-diethylcyclopenta-2,4-dien-3-yl]benzene;

1-methylsulfonyl-4-[4-(4-fluorophenyl)-1,1-bis(hydroxymethyl)cyclopenta-2,4-dien-3-yl]benzene;
1-methylsulfonyl-4-[4-(4-fluorophenyl)-1,1-bis(methoxycarbonyl)cyclopenta-2,4-alien-3-yl]benzene;
1-methylsulfonyl-4-[4-(4-fluorophenyl)-1,1-difluorocyclopenta-2,4-dien-3-yl]benzene;
1-methylsulfonyl-4-[4-(4-fluorophenyl)-1,1-bis(trifluoromethyl)cyclopenta-2,4-dien-3-yl]benzene;
1-methylsulfonyl-4-[4-(4-fluorophenyl)-1,1-bis(fluoromethyl)cyclopenta-2,4-dien-3-yl]benzene;
1-methylsulfonyl-4-[4-(4-chlorophenyl)-1,1-dimethylcyclopenta-2,4-dien-3-yl]benzene;
1-methylsulfonyl-4-[4-(4-chlorophenyl)-1,1-diethylcyclopenta-2,4-dien-3-yl]benzene;
1-methylsulfonyl-4-[4-(4-chlorophenyl)-1,1-bis(hydroxymethyl)cyclopenta-2,4-dien-3-yl]benzene;
1-methylsulfonyl-4-[4-(4-chlorophenyl)-1,1-bis(methoxycarbonyl)cyclopenta-2,4-dien-3-yl]benzene;
1-methylsulfonyl-4-[4-(4-chlorophenyl)-1,1-difluorocyclopenta-2,4-dien-3-yl]benzene;
1-methylsulfonyl-4-[4-(4-chlorophenyl)-1,1-bis(trifluoromethyl)cyclopenta-2,4-dien-3-yl]benzene;
1-methylsulfonyl-4-[4-(4-chlorophenyl)-1,1-bis(fluoromethyl)cyclopenta-2,4-dien-3-yl]benzene;
1-methylsulfonyl-4-[4-(4-trifluoromethylphenyl)-1,1-dimethylcyclopenta-2,4-dien-3-yl]benzene;
1-methylsulfonyl-4-[4-(4-trifluoromethylphenyl)-1,1-diethylcyclopenta-2,4-dien-3-yl]benzene;
1-methylsulfonyl-4-[4-(4-trifluoromethylphenyl)-1,1-bis(hydroxymethyl)cyclopenta-2,4-dien-3-yl]benzene;
1-methylsulfonyl-4-[4-(4-trifluoromethylphenyl)-1,1-bis(methoxycarbonyl)cyclopenta-2,4-dien-3-yl]benzene;
1-methylsulfonyl-4-[4-(4-trifluoromethylphenyl)-1,1-difluorocyclopenta-2,4-dien-3-yl]benzene;
1-methylsulfonyl-4-[4-(4-trifluoromethylphenyl)-1,1-bis(trifluoromethyl)cyclopenta-2,4-dien-3-yl]benzene;
1-methylsulfonyl-4-[4-(4-trifluoromethylphenyl)-1,1-bis(fluoromethyl)cyclopenta-2,4-dien-3-yl]benzene;
4-[4-(4-fluorophenyl)-1,1-dimethylcyclopenta-2,4-diene-3-yl]benzenesulfonamide;
4-[4-(4-fluorophenyl)-1,1-diethylcyclopenta-2,4-diene-3-yl]benzenesulfonamide;
4-[4-(4-fluorophenyl)-1,1-bis(hydroxymethyl)cyclopenta-2,4-diene-3-yl]benzenesulfonamide;
4-[4-(4-fluorophenyl)-1,1-bis(methoxycarbonyl)cyclopenta-2,4-diene-3-yl]benzenesulfonamide;
4-[4-(4-fluorophenyl)-1,1-difluorocyclopenta-2,4-diene-3-yl]benzenesulfonamide;
4-[4-(4-fluorophenyl)-1,1-bis(trifluoromethyl)cyclopenta-2,4-diene-3-yl]benzenesulfonamide;
4-[4-(4-fluorophenyl)-1,1-bis(fluoromethyl)cyclopenta-2,4-diene-3-yl]benzenesulfonamide;
4-[4-(4-chlorophenyl)-1,1-dimethylcyclopenta-2,4-diene-3-yl]benzenesulfonamide;
4-[4-(4-chlorophenyl)-1,1-diethylcyclopenta-2,4-diene-3-yl]benzenesulfonamide;
4-[4-(4-chlorophenyl)-1,1-bis(hydroxymethyl)cyclopenta-2,4-diene-3-yl]benzenesulfonamide;
4-[4-(4-chlorophenyl)-1,1-bis(methoxycarbonyl)cyclopenta-2,4-diene-3-yl]benzenesulfonamide;
4-[4-(4-chlorophenyl)-1,1-difluorocyclopenta-2,4-diene-3-yl]benzenesulfonamide;
4-[4-(4-chlorophenyl)-1,1-bis(trifluoromethyl)cyclopenta-2,4-diene-3-yl]benzenesulfonamide;
4-[4-(4-chlorophenyl)-1,1-bis(fluoromethyl)cyclopenta-2,4-diene-3-yl]benzenesulfonamide;
4-[4-(4-trifluoromethylphenyl)-1,1-dimethylcyclopenta-2,4-diene-3-yl]benzenesulfonamide;
4-[4-(4-trifluoromethylphenyl)-1,1-diethylcyclopenta-2,4-diene-3-yl]benzenesulfonamide;
4-[4-(4-trifluoromethylphenyl)-1,1-bis(hydroxymethyl)cyclopenta-2,4-diene-3-yl]benzenesulfonamide;
4-[4-(4-trifluoromethylphenyl)-1,1-bis(methoxycarbonyl)cyclopenta-2,4-diene-3-yl]benzenesulfonamide;
4-[4-(4-trifluoromethylphenyl)-1,1-difluorocyclopenta-2,4-diene-3-yl]benzenesulfonamide;
4-[4-(4-trifluoromethylphenyl)-1,1-bis(trifluoromethyl)cyclopenta-2,4-diene-3-yl]benzenesulfonamide;
4-[4-(4-trifluoromethylphenyl)-1,1-bis(fluoromethyl)cyclopenta-2,4-diene-3-yl]benzenesulfonamide;
1-methylsulfonyl-4-[4-(4-fluorophenyl)-1-methylcyclopenta-2,4-dien-3-yl]benzene;
1-methylsulfonyl-4-[4-(4-fluorophenyl)-1-ethylcyclopenta-2,4-dien-3-yl]benzene;
1-methylsulfonyl-4-[4-(4-fluorophenyl)-1-(hydroxymethyl)cyclopenta-2,4-dien-3-yl]benzene;
1-methylsulfonyl-4-[4-(4-fluorophenyl)-1-(methoxycarbonyl)cyclopenta-2,4-dien-3-yl]benzene;
1-methylsulfonyl-4-[4-(4-fluorophenyl)-1-fluorocyclopenta-2,4-dien-3-yl]benzene;
1-methylsulfonyl-4-[4-(4-fluorophenyl)-1-(trifluoromethyl)cyclopenta-2,4-dien-3-yl]benzene;
1-methylsulfonyl-4-[4-(4-fluorophenyl)-1-carboxycyclopenta-2,4-dien-3-yl]benzene;
1-methylsulfonyl-4-[4-(4-fluorophenyl)-1-(fluoromethyl)cyclopenta-2,4-dien-3-yl]benzene;
1-methylsulfonyl-4-[4-(4-trifluoromethylphenyl)-1-methylcyclopenta-2,4-dien-3-yl]benzene;
1-methylsulfonyl-4-[4-(4-trifluoromethylphenyl)-1-ethylcyclopenta-2,4-dien-3-yl]benzene;
1-methylsulfonyl-4-[4-(4-trifluoromethylphenyl )-1-(hydroxymethyl)cyclopenta-2,4-dien-3-yl]benzene;
1-methylsulfonyl-4-[4-(4-trifluoromethylphenyl)-1-(methoxycarbonyl)cyclopenta-2,4-dien-3-yl]benzene;
1-methylsulfonyl-4-[4-(4-trifluoromethylphenyl)-1-fluorocyclopenta-2,4-dien-3-yl]benzene;
1-methylsulfonyl-4-[4-(4-trifluoromethylphenyl)-1-(trifluoromethyl)cyclopenta-2,4-dien-3-yl]benzene;
1-methylsulfonyl-4-[4-(4-trifluoromethylphenyl)-1-carboxycyclopenta-2,4-dien-3-yl]benzene;
1-methylsulfonyl-4-[4-(4-trifluoromethylphenyl)-1-(fluoromethyl)cyclopenta-2,4-dien-3-yl]benzene;
4-[4-(4-fluorophenyl)-1-methylcyclopenta-2,4-dien-3-yl]benzenesulfonamide;
4-[4-(4-fluorophenyl)-1-ethylcyclopenta-2,4-dien-3-yl]benzenesulfonamide;
4-[4-(4-fluorophenyl)-1-(hydroxymethyl)cyclopenta-2,4-dien-3-yl]benzenesulfonamide;
4-[4-(4-fluorophenyl)-1-(methoxycarbonyl)cyclopenta-2,4-dien-3-yl]benzenesulfonamide;
4-[4-(4-fluorophenyl)-1-fluorocyclopenta-2,4-dien-3-yl]benzenesulfonamide;
4-[4-(4-fluorophenyl)-1-(trifluoromethyl)cyclopenta-2,4-dien-3-yl]benzenesulfonamide;
4-[4-(4-fluorophenyl)-1-carboxycyclopenta-2,4-dien-3-yl]benzenesulfonamide;
4-[4-(4-fluorophenyl)-1-(fluoromethyl)cyclopenta-2,4-dien-3-yl]benzenesulfonamide;
4-[4-(4-trifluoromethylphenyl)-1-methylcyclopenta-2,4-dien-3-yl]benzenesulfonamide;

4-[4-(4-trifluoromethylphenyl)-1-ethylcyclopenta-2,4-dien-3-yl]benzenesulfonamide;

4-[4-(4-trifluoromethylphenyl)-1-(hydroxymethyl)cyclopenta-2,4-dien-3-yl]benzenesulfonamide;

4-[4-(4-trifluoromethylphenyl)-1-(methoxycarbonyl)cyclopenta-2,4-dien-3-yl]benzenesulfonamide;

4-[4-(4-trifluoromethylphenyl)-1-fluorocyclopenta-2,4-dien-3-yl]benzenesulfonamide;

4-[4-(4-trifluoromethylphenyl)-1-(trifluoromethyl)cyclopenta-2,4-dien-3-yl]benzenesulfonamide;

4-[4-(4-trifluoromethylphenyl)-1-carboxycyclopenta-2,4-dien-3-yl]benzenesulfonamide; and 4-[4-(4-trifluoromethylphenyl)-1-(fluoromethyl)cyclopenta-2,4-dien-3-yl]benzenesulfonamide.

Within Formula I there is a second subclass of compounds of high interest represented by Formula III:

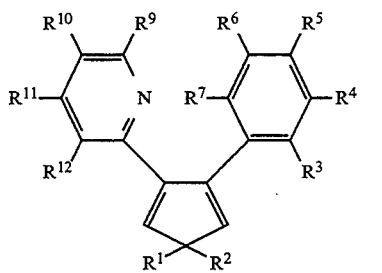

wherein each of $R^1$ and $R^2$ is independently selected from hydrido, alkyl, hydroxyalkyl, halo, haloalkyl, alkoxycarbonyl and carboxyl; and wherein each of $R^3$ through $R^7$ and $R^9$ through $R^{12}$ is independently selected from hydrido, halo, alkyl, alkylthio, cyano, hydroxyl, mercapto, haloalkyl, alkoxy, haloalkoxy, hydroxyalkyl, alkoxyalkyl, alkylsulfonyl, haloalkylsulfonyl and sulfamyl;

or a pharmaceutically-acceptable salt thereof.

A preferred class of compounds consists of those compounds of Formula III wherein each of $R^1$ and $R^2$ is independently selected from hydrido, lower alkyl, lower hydroxyalkyl, halo, lower haloalkyl, lower alkoxycarbonyl and carboxyl; and wherein each of $R^3$ through $R^7$ and $R^9$ through $R^{12}$ is independently selected from hydrido, halo, lower alkyl, lower alkylthio, cyano, hydroxyl, mercapto, lower haloalkyl, lower haloalkoxy, lower alkoxy, lower hydroxyalkyl, lower alkoxyalkyl, lower alkylsulfonyl, lower haloalkylsulfonyl and sulfamyl.

A class of compounds of particular interest consists of those compounds of Formula III wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^7$ and $R^9$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, hydroxyl, mercapto, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, trifluoromethylsulfonyl and sulfamyl.

A family of specific compounds of particular interest within Formula III consists of compounds and pharmaceutically-acceptable salts thereof as follows:

2-[4-[4-(methylsulfonyl) phenyl]cyclopenta-2,4-dien-3-yl]pyridine;

5-fluoro-2-[4-[4-(methylsulfonyl) phenyl]cyclopenta-2,4-dien-3-yl]pyridine;

5-chloro-2-[4-[4-(methylsulfonyl) phenyl]cyclopenta-2,4-dien-3-yl]pyridine;

5-methyl-2-[4-[4-(methylsulfonyl) phenyl]cyclopenta-2,4-dien-3-yl]pyridine;

5-cyano-2-[4-[4-(methylsulfonyl)phenyl]cyclopenta-2,4-dien-3-yl]pyridine;

5-trifluoromethyl-2-[4-[4-(methylsulfonyl) phenyl]cyclopenta-2,4-dien-3-yl]pyridine;

4-[4-(pyrid-2-yl)cyclopenta-2,4-dien-3-yl]benzenesulfonamide;

4-[4-(5-fluoropyrid-2-yl)cyclopenta-2,4-dien-3-yl]benzenesulfonamide;

4-[4-(5-chloropyrid-2-yl)cyclopenta-2,4-dien-3-yl]benzenesulfonamide;

4-[4-(5-methylpyrid-2-yl)cyclopenta-2,4-dien-3-yl]benzenesulfonamide;

4-[4-(5-cyanopyrid-2-yl)cyclopenta-2,4-dien-3-yl]benzenesulfonamide;

4-[4-(5-trifluoromethylpyrid-2-yl)cyclopenta-2,4-dien-3-yl]benzenesulfonamide;

5-fluoro-2-[4-[4-(methylsulfonyl)phenyl]-1-methylcyclopenta-2,4-dien-3-yl]pyridine;

5-fluoro-2-[4-[4-(methylsulfonyl)phenyl]-1-ethylcyclopenta-2,4-dien-3-yl]pyridine;

5-fluoro-2-[4-[4-(methylsulfonyl)phenyl]-1-(hydroxymethyl)cyclopenta-2,4-dien-3-yl]pyridine;

5-fluoro-2-[4-[4-(methylsulfonyl)phenyl]-1-(methoxycarbonyl)cyclopenta-2,4-dien-3-yl]pyridine;

5-fluoro-2-[4-[4-(methylsulfonyl)phenyl]-1-fluorocyclopenta-2,4-dien-3-yl]pyridine;

5-fluoro-2-[4-[4-(methylsulfonyl)phenyl]-1-(trifluoromethyl)cyclopenta-2,4-dien-3-yl]pyridine;

5-fluoro-2-[4-[4-(methylsulfonyl)phenyl]-1-carboxycyclopenta-2,4-dien-3-yl]pyridine;

5-fluoro-2-[4-[4-(methylsulfonyl)phenyl]-1-(fluoromethyl)cyclopenta-2,4-dien-3-yl]pyridine;

5-trifluoromethyl-2-[4-[4-(methylsulfonyl)phenyl]-1-methylcyclopenta-2,4-dien-3-yl]pyridine;

5-trifluoromethyl-2-[4-[4-(methylsulfonyl)phenyl]-1-ethylcyclopenta-2,4-dien-3-yl]pyridine;

5-trifluoromethyl-2-[4-[4-(methylsulfonyl)phenyl]-1-(hydroxymethyl)cyclopenta-2,4-dien-3-yl]pyridine;

5-trifluoromethyl-2-[4-[4-(methylsulfonyl)phenyl]-1-(methoxycarbonyl)cyclopenta-2,4-dien-3-yl]pyridine;

5-trifluoromethyl-2-[4-[4-(methylsulfonyl)phenyl]-1-fluorocyclopenta-2,4-dien-3-yl]pyridine;

5-trifluoromethyl-2-[4-[4-(methylsulfonyl)phenyl]-1-(trifluoromethyl)cyclopenta-2,4-dien-3-yl]pyridine;

5-trifluoromethyl-2-[4-[4-(methylsulfonyl)phenyl]-1-carboxycyclopenta-2,4-dien-3-yl]pyridine;

5-trifluoromethyl-2-[4-[4-(methylsulfonyl)phenyl]-1-(fluoromethyl)cyclopenta-2,4-dien-3-yl]pyridine;

4-[4-(5-fluoropyrid-2-yl)-1-methylcyclopenta-2,4-dien-3-yl]benzenesulfonamide;
4-[4-(5-fluoropyrid-2-yl)-1-ethylcyclopenta-2,4-dien-3-yl]benzenesulfonamide;
4-[4-(5-fluoropyrid-2-yl)-1-(hydroxymethyl)cyclopenta-2,4-dien-3-yl]benzenesulfonamide;
4-[4-(5-fluoropyrid-2-yl)-1-(methoxycarbonyl)cyclopenta-2,4-dien-3-yl]benzenesulfonamide;
4-[4-(5-fluoropyrid-2-yl)-1-fluorocyclopenta-2,4-dien-3-yl]benzenesulfonamide;
4-[4-(5-fluoropyrid-2-yl)-1-(trifluoromethyl)cyclopenta-2,4-dien-3-yl]benzenesulfonamide;
4-[4-(5-fluoropyrid-2-yl)-1-carboxycyclopenta-2,4-dien-3-yl]benzenesulfonamide;
4-[4-(5-fluoropyrid-2-yl)-1-(fluoromethyl)cyclopenta-2,4-dien-3-yl]benzenesulfonamide;
4-[4-(5-trifluoromethylpyrid-2-yl)-1-methylcyclopenta-2,4-dien-3-yl]benzenesulfonamide;
4-[4-(5-trifluoromethylpyrid-2-yl)-1-ethylcyclopenta-2,4-dien-3-yl]benzenesulfonamide;
4-[4-(5-trifluoromethylpyrid-2-yl)-1-(hydroxymethyl)-cyclopenta-2,4-dien-3-yl]benzenesulfonamide;
4-[4-(5-trifluoromethylpyrid-2-yl)-1-(methoxycarbonyl)cyclopenta-2,4-dien-3-yl]benzenesulfonamide;
4-[4-(5-trifluoromethylpyrid-2-yl)-1-fluorocyclopenta-2,4-dien-3-yl]benzenesulfonamide;
4-[4-(5-trifluoromethylpyrid-2-yl)-1-(trifluoromethyl)-cyclopenta-2,4-dien-3-yl]benzenesulfonamide;
4-[4-(5-trifluoromethylpyrid-2-yl)-1-carboxycyclopenta-2,4-dien-3-yl]benzenesulfonamide;
4-[4-(5-trifluoromethylpyrid-2-yl)-1-(fluoromethyl)cyclopenta-2,4-dien-3-yl]benzenesulfonamide;
4-fluoro-2-[4-[4-(methylsulfonyl)phenyl]-1,1-dimethylcyclopenta-2,4-dien-3-yl]pyridine;
5-fluoro-2-[4-[4-(methylsulfonyl)phenyl]-1,1-diethylcyclopenta-2,4-dien-3-yl]pyridine;
5-fluoro-2-[4-[4-(methylsulfonyl)phenyl]-1,1 -bis(hydroxymethyl)cyclopenta-2,4-dien-3-yl]pyridine;
5-fluoro-2-[4-[4-(methylsulfonyl)phenyl]-1,1-bis(methoxycarbonyl)cyclopenta-2,4-dien-3-yl]pyridine;
5-fluoro-2-[4-[4-(methylsulfonyl)phenyl]-1,1-difluorocyclopenta-2,4-dien-3-yl]pyridine;
5-fluoro-2-[4-[4-(methylsulfonyl)phenyl]-1,1-bis(trifluoromethyl)cyclopenta-2,4-dien-3-yl]pyridine;
5-fluoro -2-[4-[4-(methylsulfonyl)phenyl]-1,1-bis(-fluoromethyl)cyclopenta-2,4-dien-3-yl]pyridine;
5-trifluoromethyl-2-[4-[4-(methylsulfonyl)phenyl]-1,1-dimethylcyclopenta-2,4-dien-3-yl]pyridine;
5-trifluoromethyl-2-[4-[4-(methylsulfonyl)phenyl]-1,1-diethylcyclopenta-2,4-dien-3-yl]pyridine;
5-trifluoromethyl-2-[4-[4-(methylsulfonyl)phenyl]-1,1-bis(hydroxymethyl)cyclopenta-2,4-dien-3-yl]pyridine;
5-trifluoromethyl-2-[4-[4-(methylsulfonyl)phenyl]-1,1-bis(methoxycarbonyl)cyclopenta-2,4-dien-3-yl]pyridine;
5-trifluoromethyl-2-[4-[4-(methylsulfonyl)phenyl]-1,1-difluorocyclopenta-2,4-dien-3-yl]pyridine;
5-trifluoromethyl-2-[4-[4-(methylsulfonyl)phenyl]-1,1-bis(trifluoromethyl)cyclopenta-2,4-dien-3-yl]pyridine;
5-trifluoromethyl-2-[4-[4-(methylsulfonyl)phenyl]-1,1-bis(fluoromethyl)cyclopenta-2,4-dien-3-yl]pyridine;
4-[4-(5-fluoropyrid-2-yl)-1,1-dimethylcyclopenta-2,4-dien-3-yl]benzenesulfonamide;
4-[4-(5-fluoropyrid-2-yl)-1,1-diethylcyclopenta-2,4-dien-3-yl]benzenesulfonamide;
4-[4-(5-fluoropyrid-2-yl)-1,1-bis(hydroxymethyl)cyclopenta-2,4-dien-3-yl]benzenesulfonamide;
4-[4-(5-fluoropyrid-2-yl)-1,1-bis(methoxycarbonyl)cyclopenta-2,4-dien-3-yl]benzenesulfonamide;
4-[4-(5-fluoropyrid-2-yl)-1,1-difluorocyclopenta-2,4-dien-3-yl]benzenesulfonamide;
4-[4-(5-fluoropyrid-2-yl)-1,1-bis(trifluoromethyl)cyclopenta-2,4-dien-3-yl]benzenesulfonamide;
4-[4-(5-fluoropyrid-2-yl)-1,1-bis(fluoromethyl)cyclopenta-2,4-dien-3-yl]benzenesulfonamide;
4-[4-(5-trifluoromethylpyrid-2-yl)-1,1-dimethylcyclopenta-2,4-dien-3-yl]benzenesulfonamide;
4-[4-(5-trifluoromethylpyrid-2-yl)-1,1-diethylcyclopenta-2,4-dien-3-yl]benzenesulfonamide;
4-[4-(5-trifluoromethylpyrid-2-yl)-1,1-bis(hydroxymethyl)cyclopenta- 2,4-dien-3-yl]benzenesulfonamide;
4-[4-(5-trifluoromethylpyrid-2-yl)-1,1-bis(methoxycarbonyl)cyclopenta-2,4-dien-3-yl]benzenesulfonamide;
4-[4-(5-trifluoromethylpyrid-2-yl)-1,1-difluorocyclopenta-2,4-dien-3-yl]benzenesulfonamide;
4-[4-(5-trifluoromethylpyrid-2-yl)-1,1-bis(trifluoromethyl)cyclopenta-2,4-dien-3-yl]benzenesulfonamide;
4-[4-(5-trifluoromethylpyrid-2-yl)-1,1-bis(fluoromethyl)cyclopenta-2,4-dien-3-yl]benzenesulfonamide;
2-(4-phenylcyclopenta-2,4-dien-3-yl)-5-(methylsulfonyl)pyridine;
2-[4-(4-fluorophenyl)cyclopenta-2,4-dien-3-yl)-5-(methylsulfonyl)pyridine;
2-[4-(4-chlorophenyl)cyclopenta-2,4-dien-3-yl)-5-(methylsulfonyl)pyridine;
2-[4-(4-methylphenyl)cyclopenta-2,4-dien-3-yl)-5-(methylsulfonyl)pyridine;
2-[4-(4-cyanophenyl)cyclopenta-2,4-dien-3-yl)-5-(methylsulfonyl)pyridine;
2-[4-(4-trifluoromethylphenyl)cyclopenta-2,4-dien-3-yl)-5-(methylsulfonyl)pyridine;
2-(4-phenylcyclopenta-2,4-dien-3-yl)-5-pyridinesulfonamide;
2-[4-(4-fluorophenyl)cyclopenta-2,4-dien-3-yl)-5-pyridinesulfonamide;
2-[4-(4-chlorophenyl)cyclopenta-2,4-dien-3-yl)-5-pyridinesulfonamide;
2-[4-(4-methylphenyl)cyclopenta-2,4-dien-3-yl)-5-pyridinesulfonamide;
2-[4-(4-cyanophenyl)cyclopenta-2,4-dien-3-yl)-5-pyridinesulfonamide;
2-[4-(4-trifluoromethylphenyl)cyclopenta-2,4-dien-3-yl)-5-pyridinesulfonamide;
2-[4-(4-fluorophenyl)-1-methylcyclopenta- 2,4-dien-3-yl)-5-(methylsulfonylpyridine;
2-[4-(4-fluorophenyl)-1-ethylcyclopenta-2,4-dien-3-yl)-5-(methylsulfonylpyridine;
2-[4-(4-fluorophenyl)-1-(hydroxymethyl)cyclopenta-2,4-dien-3-yl)-5-(methylsulfonyl)pyridine;
2-[4-(4-fluorophenyl)-1-(methoxycarbonyl)cyclopenta-2,4-dien-3-yl)-5-(methylsulfonyl)pyridine;
2-[4-(4-fluorophenyl)-1-fluorocyclopenta-2,4-dien-3-yl)-5-(methylsulfonyl)pyridine;
2-[4-(4-fluorophenyl)-1-(trifluoromethyl)cyclopenta-2,4-dien-3-yl)-5-(methylsulfonyl)pyridine;
2-[4-(4-fluorophenyl)-1-carboxycyclopenta-2,4-dien-3-yl)-5-(methylsulfonyl)pyridine;
2-[4-(4-fluorophenyl)-1-(fluoromethyl)cyclopenta-2,4-dien-3-yl)-5-(methylsulfonyl)pyridine;
2-[4-(4-trifluoromethylphenyl)-1-methylcyclopenta-2,4-dien-3-yl)-5-(methylsulfonyl)pyridine;
2-[4-(4-trifluoromethylphenyl)-1-ethylcyclopenta-2,4-dien-3-yl)-5-(methylsulfonylpyridine;

2-[4-(4-trifluoromethylphenyl)-1-(hydroxymethyl)cyclopenta-2,4-dien-3-yl)-5-(methylsulfonyl)pyridine;
2-[4-(4- trifluoromethylphenyl)-1-(methoxycarbonyl)cyclopenta-2,4-dien-3-yl)-5(methylsulfonyl)pyridine;
2-[4-(4-trifluoromethylphenyl)-1-fluorocyclopenta-2,4-dien-3-yl)-5-(methylsulfonyl)pyridine;
2-[4-(4-trifluoromethylphenyl)-1-(trifluoromethyl)cyclopenta-2,4-alien-3-yl)-5-(methylsulfonyl)pyridine;
2-[4-(4-trifluoromethylphenyl)-1-carboxycyclopenta-2,4-dien-3-yl)-5-(methylsulfonyl)pyridine;
2-[4-(4-trifluoromethylphenyl)-1-(fluoromethyl)cyclopenta-2,4-dien-3-yl)-5-(methylsulfonyl)pyridine;
2-[4-(4-fluorophenyl)-1-methylcyclopenta-2,4-dien-3-yl]-5-pyridinesulfonamide;
2-[4-(4-fluorophenyl)-1-ethylcyclopenta-2,4-dien-3-yl]-5-pyridinesulfonamide;
2-[4-(4-fluorophenyl)-1-(hydroxymethyl)cyclopenta-2,4-dien-3-yl]-5-pyridinesulfonamide;
2-[4-(4-fluorophenyl)-1-(methoxycarbonyl)cyclopenta-2,4-dien-3-yl]-5-pyridinesulfonamide;
2-[4-(4-fluorophenyl)-1-fluorocyclopenta-2,4-dien-3-yl]-5-pyridinesulfonamide;
2-[4-(4-fluorophenyl)-1-(trifluoromethyl)cyclopenta-2,4-dien-3-yl]-5-pyridinesulfonamide;
2-[4-(4-fluorophenyl)-1-carboxycyclopenta-2,4-dien-3-yl]-5-pyridinesulfonamide;
2-[4-(4-fluorophenyl)-1-(fluoromethyl)cyclopenta-2,4-dien-3-yl]-5-pyridinesulfonamide;
2-[4-(4-trifluoromethylphenyl)-1-methylcyclopenta-2,4-dien-3-yl]-5-pyridinesulfonamide;
2-[4-(4-trifluoromethylphenyl)-1-ethylcyclopenta-2,4-dien-3-yl]-5-pyridinesulfonamide;
2-[4-(4- trifluoromethylphenyl)-1-(hydroxymethyl)cyclopenta-2,4-dien-3-yl]-5-pyridinesulfonamide;
2-[4-(4-trifluoromethylphenyl)-1-(methoxycarbonyl)cyclopenta-2,4-dien-3-yl]-5-pyridinesulfonamide;
2-[4-(4-trifluoromethylphenyl)-1-fluorocyclopenta-2,4-dien-3-yl]-5-pyridinesulfonamide;
2-[4-(4-trifluoromethylphenyl)-1-(trifluoromethyl)cyclopenta-2,4-dien-3-yl]-5-pyridinesulfonamide;
2-[4-(4-trifluoromethylphenyl)-1-carboxycyclopenta-2,4-dien-3-yl]-5-pyridinesulfonamide;
2-[4-(4-trifluoromethylphenyl)-1-(fluoromethyl)cyclopenta-2,4-dien-3-yl]-5-pyridinesulfonamide;
2-[4-(4-fluorophenyl)-1,1-dimethylcyclopenta-2,4-dien-3-yl]-5-(methylsulfonyl)pyridine;
2-[4-(4-fluorophenyl)-1,1-diethylcyclopenta-2,4-dien-3-yl]-5-(methylsulfonyl)pyridine;
2-[4-(4-fluorophenyl)-1,1-bis(hydroxymethyl)cyclopenta-2,4-dien-3-yl]-5-(methylsulfonyl)pyridine;
2-[4-(4-fluorophenyl)-1,1-bis(methoxycarbonyl)cyclopenta- 2,4-dien-3-yl]-5-(methylsulfonyl)pyridine;
2-[4-(4-fluorophenyl)-1,1-difluorocyclopenta-2,4-dien-3-yl]-5-(methylsulfonyl)pyridine;
2-[4-(4-fluorophenyl)-1,1-bis(trifluoromethyl)cyclopenta-2,4-dien-3-yl]-5-(methylsulfonyl)pyridine;
2-[4-(4-fluorophenyl)-1,1-bis(fluoromethyl)cyclopenta-2,4-dien-3-yl]-5-(methylsulfonyl)pyridine;
2-[4-(4-trifluoromethylphenyl)-1,1-dimethylcyclopenta-2,4-dien-3-yl]-5-(methylsulfonyl)pyridine;
2-[4-(4-trifluoromethylphenyl)-1,1-diethylcyclopenta-2,4-dien-3-yl]-5-(methylsulfonyl)pyridine;
2-[4-(4-trifluoromethylphenyl)-1,1-bis(hydroxymethyl)cyclopenta-2,4-dien-3-yl]-5-(methylsulfonyl)pyridine;
2-[4-(4-trifluoromethylphenyl)-1,1-bis(methoxycarbonyl)cyclopenta-2,4-dien-3-yl]-5 -(methylsulfonyl)pyridine;
2-[4-(4-trifluoromethylphenyl)-1,1-difluorocyclopenta-2,4-dien-3-yl]-5-(methylsulfonyl)pyridine;
2-[4-(4-trifluoromethylphenyl)-1,1-bis(trifluoromethyl)cyclopenta-2,4-dien-3-yl]-5-(methylsulfonyl)pyridine;
2-[4-(4-trifluoromethylphenyl)-1,1-bis(fluoromethyl)cyclopenta-2,4-dien-3-yl]-5-(methylsulfonyl)pyridine;
2-[4-(4-fluorophenyl)-1,1-dimethylcyclopenta-2,4-dien-3-yl]-5-pyridinesulfonamide;
2-[4-(4-fluorophenyl)-1,1-diethylcyclopenta-2,4-dien-3-yl]-5-pyridinesulfonamide;
2-[4-(4-fluorophenyl)-1,1-bis(hydroxymethyl)cyclopenta-2,4-dien-3-yl]-5-pyridinesulfonamide;
2-[4-(4-fluorophenyl)-1,1-bis(methoxycarbonyl)cyclopenta-2,4-dien-3-yl]-5-pyridinesulfonamide;
2-[4-(4-fluorophenyl)-1,1-difluorocyclopenta-2,4-dien-3-yl]-5-pyridinesulfonamide;
2-[4-(4-fluorophenyl)-1,1-bis(trifluoromethyl)cyclopenta-2,4-dien-3-yl]-5-pyridinesulfonamide;
12-[4-(4-fluorophenyl)-1,1-bis(fluoromethyl)cyclopenta-2,4-dien-3-yl]-5-pyridinesulfonamide;
2-[4-(4-trifluoromethylphenyl)-1,1-dimethylcyclopenta-2,4-dien-3-yl]-5-pyridinesulfonamide;
2-[4-(4-trifluoromethylphenyl)-1,1-diethylcyclopenta-2,4- dien-3-yl]-5-pyridinesulfonamide;
2-[4-(4-trifluoromethylphenyl)-1,1-bis(hydroxymethyl)cyclopenta-2,4-dien-3-yl]-5-pyridinesulfonamide;
2-[4-(4-trifluoromethylphenyl)-1,1-bis(methoxycarbonyl)cyclopenta-2,4-dien-3-yl]-5-pyridinesulfonamide;
2-[4-(4-trifluoromethylphenyl)-1,1-difluorocyclopenta-2,4-dien-3-yl]-5-pyridinesulfonamide;
2-[4-(4-trifluoromethylphenyl)-1,1-bis(trifluoromethyl)cyclopenta-2,4-dien-3-yl]-5-pyridinesulfonamide; and
2-[4-(4-trifluoromethylphenyl)-1,1-bis(fluoromethyl)cyclopenta-2,4-dien-3-yl]-5-pyridinesulfonamide.

Within Formula I there is a third subclass of compounds of high interest represented by Formula IV:

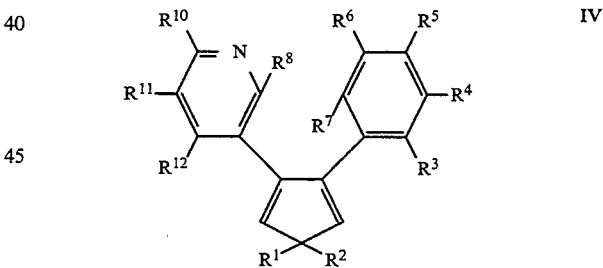

wherein each of $R^1$ and $R^2$ is independently selected from hydrido, alkyl, hydroxyalkyl, halo, haloalkyl, alkoxycarbonyl and carboxyl; and wherein each of $R^3$ through $R^8$ and $R^{10}$ through $R^{12}$ is independently selected from hydrido, halo, alkyl, alkylthio, cyano, hydroxyl, mercapto, haloalkyl, alkoxy, haloalkoxy, hydroxyalkyl, alkoxyalkyl, alkylsulfonyl, haloalkylsulfonyl and sulfamyl; or a pharmaceutically-acceptable salt or prodrug thereof.

A preferred class of compounds consists of those compounds of Formula IV wherein each of $R^1$ and $R^2$ is independently selected from hydrido, lower alkyl, lower hydroxyalkyl, halo, lower haloalkyl, lower alkoxycarbonyl and carboxyl; and wherein each of $R^3$ through $R^8$ and $R^{10}$ through $R^{12}$ is independently selected from hydrido, halo, lower alkyl, lower alkylthio, cyano, hydroxyl, mercapto, lower haloalkyl, lower haloalkoxy, lower alkoxy, lower hydroxyalkyl, lower alkoxyalkyl, lower alkylsulfonyl, lower haloalkylsulfonyl and sulfamyl.

A more preferred class of compounds consists of those compounds of Formula IV wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^8$ and $R^{10}$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, hydroxyl, mercapto, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, trifluoromethylsulfonyl and sulfamyl.

A family of specific compounds of particular interest within Formula IV consists of compounds and pharmaceutically-acceptable salts thereof as follows:

3-[4-[4-(methylsulfonyl)phenyl]cyclopenta-2,4-dien-3-yl]pyridine;
2-fluoro-5-[4-[4-(methylsulfonyl)phenyl]cyclopenta-2,4-dien-3-yl]pyridine;
2-chloro-5-[4-[4-(methylsulfonyl)phenyl]cyclopenta-2,4-dien-3-yl]pyridine;
2-methyl-5-[4-[4-(methylsulfonyl)phenyl]cyctopenta-2,4-dien-3-yl]pyridine;
2-cyano-5-[4-[4-(methylsulfonyl)phenyl]cyclopenta-2,4-dien-3-yl]pyridine;
2-trifluoromethyl-5-[4-[4-(methylsulfonyl)phenyl]cyclopenta-2,4-dien-3-yl]pyridine;
2-[4-(pyrid-3-yl)cyclopenta-2,4-dien-3-yl]benzenesulfonamide;
4-[4-(2-fluoropyrid-3-yl)cyclopenta-2,4-dien-3-yl]benzenesulfonamide;
4-[4-(2-chloropyrid-3-yl)cyclopenta-2,4-dien-3-yl]benzenesulfonamide;
4-[4-(2-methylpyrid-3-yl)cyclopenta-2,4-dien-3-yl]benzenesulfonamide;
4-[4-(2-cyanopyrid-3-yl)cyclopenta-2,4-dien-3-yl]benzenesulfonamide;
4-[4-(2-trifluoromethylpyrid-3-yl)cyclopenta-2,4-dien-3-yl]benzenesulfonamide;
2-fluoro-5-[4-[4-(methylsulfonyl)phenyl]-4-methylcyclopenta-2,4-dien-3-yl]pyridine;
2-fluoro-5-[4-[4-(methylsulfonyl)phenyl]-4-ethylcyclopenta-2,4-dien-3-yl]pyridine;
2-fluoro-5-[4-[4-(methylsulfonyl)phenyl]-4(hydroxymethyl)cyclopenta-2,4-dien-3-yl]pyridine;
2-fluoro-5-[4-[4-(methylsulfonyl)phenyl]-4(methoxycarbonyl)cyclopenta-2,4-dien-3-yl]pyridine;
2-fluoro-5-[4-[4-(methylsulfonyl)phenyl]-4-fluorocyclopenta-2,4-dien-3-yl]pyridine;
2-fluoro-5-[4-[4-(methylsulfonyl)phenyl]-4-(trifluoromethyl)cyclopenta-2,4-dien-3-yl]pyridine;
2-fluoro-5-[4-[4-(methylsulfonyl)phenyl]-4-carboxycyclopenta-2,4-dien-3-yl]pyridine;
2-fluoro-5-[4-[4-(methylsulfonyl)phenyl]-4-(fluoromethyl)cyclopenta-2,4-dien-3-yl]pyridine;
2-trifluoromethyl-5-[4-[4-(methylsulfonyl)phenyl]-4-methylcyclopenta-2,4-dien-3-yl]pyridine;
2-trifluoromethyl-5-[4-[4-(methylsulfonyl)phenyl]-4-ethylcyclopenta-2,4-dien-3-yl]pyridine;
2-trifluoromethyl-5-[4-[4-(methylsulfonyl)phenyl]-4-(hydroxymethyl)cyclopenta-2,4-dien-3-yl]pyridine;
2-trifluoromethyl-5-[4-[4-(methylsulfonyl)phenyl]-4(methoxycarbonyl)cyclopenta-2,4-dien-3-yl]pyridine;
2-trifluoromethyl-5-[4-[4-(methylsulfonyl)phenyl]-4-fluorocyclopenta-2,4-dien-3-yl]pyridine;
2-trifluoromethyl-5-[4-[4-(methylsulfonyl)phenyl]-4-(trifluoromethyl)cyclopenta-2,4-dien-3-yl]pyridine;
2-trifluoromethyl-5-[4-[4-(methylsulfonyl)phenyl]-4-carboxycyclopenta-2,4-dien-3-yl]pyridine;
2-trifluoromethyl-5-[4-[4-(methylsulfonyl)phenyl]-4-(fluoromethyl)cyclopenta-2,4-dien-3-yl]pyridine;
4-[4-(2-fluoropyrid-5-yl)-1-methylcyclopenta-2,4-dien-3-yl]benzenesulfonamide;
4-[4-(2-fluoropyrid-5-yl)-1-ethylcyclopenta-2,4-dien-3-yl]benzenesulfonamide;
4-[4-(2-fluoropyrid-5-yl)-1-(hydroxymethyl)cyclopenta-2,4-dien-3-yl]benzenesulfonamide;
4-[4-(2-fluoropyrid-5-yl)-1-(methoxycarbonyl)cyclopenta-2,4-dien-3-yl]benzenesulfonamide;
4-[4-(2-fluoropyrid-5-yl)-1-fluorocyclopenta-2,4-dien-3-yl]benzenesulfonamide;
4-[4-(2-fluoropyrid-5-yl)-1-(trifluoromethyl)cyclopenta-2,4-dien-3-yl]benzenesulfonamide;
4-[4-(2-fluoropyrid-5-yl)-1-carboxycyclopenta-2,4-dien-3-yl]benzenesulfonamide;
4-[4-(2-fluoropyrid-5-yl)-1-(fluoromethyl)cyctopenta-2,4-dien-3-yl]benzenesulfonamide;
4-[4-(2-trifluoromethylpyrid-5-yl)-1-methylcyclopenta-2,4-dien-3-yl]benzenesulfonamide;
4-[4-(2-trifluoromethylpyrid-5-yl)-1-ethylcyclopenta-2,4-dien-3-yl]benzenesulfonamide;
4-[4-(2-trifluoromethylpyrid-5-yl)-1-(hydroxymethyl)cyclopenta-2,4-dien-3-yl]benzenesulfonamide;
4-[4-(2-trifluoromethylpyrid-5-yl)-1-(methoxycarbonyl)cyclopenta-2,4-dien-3-yl]benzenesulfonamide;
4-[4-(2-trifluoromethylpyrid-5-yl)-1-fluorocyclopenta-2,4-dien-3-yl]benzenesulfonamide;
4-[4-(2-trifluoromethylpyrid-5-yl)-1-(trifluoromethyl)cyclopenta-2,4-dien-3-yl]benzenesulfonamide;
4-[4-(2-trifluoromethylpyrid-5-yl)-1-carboxycyclopenta-2,4-dien-3-yl]benzenesulfonamide;
4-[4-(2-trifluoromethylpyrid-5-yl)-1-(fluoromethyl)cyclopenta-2,4-dien-3-yl]benzenesulfonamide;
2-fluoro-5-[4-[4-(methylsulfonyl)phenyl]-1,1-dimethylcyclopenta-2,4-dien-3-yl]pyridine;
2-fluoro-5-[4-[4-(methylsulfonyl)phenyl]-1,1-diethylcyclopenta-2,4-dien-3-yl]pyridine;
2-fluoro-5-[4-[4-(methylsulfonyl)phenyl]-1,1-bis(hydroxymethyl)cyclopenta-2,4-dien-3-yl]pyridine;
2-fluoro-5-[4-[4-(methylsulfonyl)phenyl]-1,1-bis(methoxycarbonyl)cyclopenta-2,4-dien-3yl]pyridine;
2-fluoro-5-[4-[4-(methylsulfonyl)phenyl]-1,1-difluorocyclopenta-2,4-dien-3-yl]pyridine;
2-fluoro-5-[4-[4-(methylsulfonyl)phenyl]-1,1-bis(trifluoromethyl)cyclopenta-2,4-dien-3-yl]pyridine;

2-fluoro-5-[4-[4-(methylsulfonyl)phenyl]-1,1-bis(-fluoromethyl)cyclopenta-2,4-dien-3-yl]pyridine;
2-trifluoromethyl-5-[4-[4-(methylsulfonyl)phenyl]-1,1-dimethylcyclopenta-2,4-dien-3-yl]pyridine;
2-trifluoromethyl-5-[4-[4-(methylsulfonyl)phenyl]-1,1-diethylcyclopenta-2,4-dien-3-yl]pyridine;
2-trifluoromethyl-5-[4-[4-(methylsulfonyl)phenyl]-1,1-bis(hydroxymethyl)cyclopenta-2,4-dien-3-yl]pyridine;
2-trifluoromethyl-5-[4-[4-(methylsulfonyl)phenyl]-1,1-bis(methoxycarbonyl)cyclopenta-2,4-dien-3yl]pyridine;
2-trifluoromethyl-5-[4-[4-(methylsulfonyl)phenyl]-1,1-difluorocyclopenta-2,4-dien-3-yl]pyridine;
2-trifluoromethyl-5-[4-[4-(methylsulfonyl)phenyl]-1,1-bis(trifluoromethyl)cyclopenta-2,4-dien-3-yl]pyridine;
2-trifluoromethyl-5-[4-[4-(methylsulfonyl)phenyl]-1,1-bis(fluoromethyl)cyclopenta-2,4-dien-3-yl]pyridine;
4-[4-(2-fluoropyrid-5-yl)-1,1-dimethylcyclopenta-2,4-dien-3-yl]benzenesulfonamide;
4-[4-(2-fluoropyrid-5-yl)-1,1-diethylcyclopenta-2,4-dien-3-yl]benzenesulfonamide;
4-[4-(2-fluoropyrid-5-yl)-1,1-bis(hydroxymethyl)cyclopenta-2,4-dien-3-yl]benzenesulfonamide;
4-[4-(2-fluoropyrid-5-yl)-1,1-bis(methoxycarbonyl)cyclopenta-2,4-dien-3-yl]benzenesulfonamide;
4-[4-(2-fluoropyrid-5-yl)-1,1-difluorocyctopenta-2,4-dien-3-yl]benzenesulfonamide;
4-[4-(2-fluoropyrid-5-yl)-1,1-bis(trifluoromethyl)cyclopenta-2,4-dien-3-yl]benzenesulfonamide;
4-[4-(2-fluoropyrid-5-yl)-1,1-bis(fluoromethyl)cyclopenta-2,4-dien-3-yl]benzenesulfonamide;
4-[4-(2-trifluoromethylpyrid-5-yl)-1,1-dimethylcyclopenta-2,4-dien-3-yl]benzenesulfonamide;
4-[4-(2-trifluoromethylpyrid-5-yl)-1,1-diethylcyclopenta-2,4-dien-3-yl]benzenesulfonamide;
4-[4-(2-trifluoromethylpyrid-5-yl)-1,1-bis(hydroxymethyl)cyclopenta-2,4-dien-3-yl]benzenesulfonamide;
4-[4-(2-trifluoromethylpyrid-5-yl)-1,1-bis(methoxycarbonyl)cyclopenta-2,4-dien-3-yl]benzenesulfonamide;
4-[4-(2-trifluoromethylpyrid-5-yl)-1,1-difluorocyclopenta-2,4-dien-3-yl]benzenesulfonamide;
4-[4-(2-trifluoromethylpyrid-5-yl)-1,1-bis(trifluoromethyl)cyclopenta-2,4-dien-3-yl]benzenesulfonamide;
4-[4-(2-trifluoromethylpyrid-5-yl)-1,1-bis(fluoromethyl)cyclopenta-2,4-dien-3-yl]benzenesulfonamide;
5-(4-phenylcyclopenta-2,4-dien-3-yl)-2-(methylsulfonyl)pyridine;
5-[4-(4-fluorophenyl)cyclopenta-2,4-dien-3-yl]-2-(methylsulfonyl)pyridine;
5-[4-(4-chlorophenyl)cyclopenta-2,4-dien-3-yl]-2-(methylsulfonyl)pyridine;
5-[4-(4-methylphenyl)cyclopenta-2,4-dien-3-yl]-2-(methylsulfonyl)pyridine;
5-[4-(4-cyanophenyl)cyclopenta-2,4-dien-3-yl]-2-(methylsulfonyl)pyridine;
5-[4-(4-trifluoromethylphenyl)cyclopenta-2,4-dien-3-yl]-2-(methylsulfonyl)pyridine;
5-(4-phenylcyclopenta-2,4-dien-3-yl)-2-pyridinesulfonamide;
5-[4-(4-fluorophenyl)cyclopenta-2,4-dien-3-yl]-2-pyridinesulfonamide;
5-[4-(4-chlorophenyl)cyclopenta-2,4-dien-3-yl]-2-pyridinesulfonamide;
5-[4-(4-methylphenyl)cyclopenta-2,4-dien-3-yl]-2-pyridinesulfonamide;
5-[4-(4-cyanophenyl)cyclopenta-2,4-dien-3-yl]-2-pyridinesulfonamide;
5-[4-(4-trifluoromethylphenyl)cyclopenta-2,4-dien-3-yl]-2-pyridinesulfonamide;
5-[4-(4-fluorophenyl)-1-methylcyclopenta-2,4-dien-3-yl]-2-(methylsulfonyl)pyridine;
5-[4-(4-fluorophenyl)-1-ethylcyclopenta-2,4-dien-3-yl]-2-(methylsulfonyl)pyridine;
5-[4-(4-fluorophenyl)-1-(hydroxymethyl)cyclopenta-2,4-dien-3-yl]-2-(methylsulfonyl)pyridine;
5-[4-(4-fluorophenyl)-1-(methoxycarbonyl)cyclopenta-2,4-dien-3-yl]-2-(methylsulfonyl)pyridine;
5-[4-(4-fluorophenyl)-1-(trifluoromethyl)cyclopenta-2,4-dien-3-yl]-2-(methylsulfonyl)pyridine;
5-[4-(4-fluorophenyl)-1-carboxycyclopenta-2,4-dien-3-yl]-2-(methylsulfonyl)pyridine;
5-[4-(4-fluorophenyl)-1-(fluoromethyl)cyclopenta-2,4-dien-3-yl]-2-(methylsulfonyl)pyridine;
5-[4-(4-trifluoromethylphenyl)-1-methylcyclopenta-2,4-dien-3-yl]-2-(methylsulfonyl)pyridine;
5-[4-(4-trifluoromethylphenyl)-1-ethylcyclopenta-2,4-dien-3-yl]-2-(methylsulfonyl)pyridine;
5-[4-(4-trifluoromethylphenyl)-1-(hydroxymethyl)cyclopenta-2,4-dien-3-yl]-2(methylsulfonyl)pyridine;
5-[4-(4-trifluoromethylphenyl)-1-(methoxycarbonyl)cyclopenta-2,4-dien-3-yl]-2-(methylsulfonyl)pyridine;
5-[4-(4- trifluoromethylphenyl)-1-(trifluoromethyl)cyclopenta-2,4-dien-3-yl]-2-(methylsulfonyl)pyridine;
5-[4-(4-trifluoromethylphenyl)-1-carboxycyclopenta-2,4-dien-3-yl]-2-(methylsulfonyl)pyridine;
5-[4-(4-trifluoromethylphenyl)-1-(fluoromethyl)cyclopenta-2,4-dien-3-yl]-2-(methylsulfonyl)pyridine;
5-[4-(4-fluorophenyl)-1-methylcyclopenta-2,4-dien-3-yl]-2-pyridinesulfonamide;
5-[4-(4-fluorophenyl)-1-ethylcyclopenta-2,4-dien-3-yl]-2-pyridinesulfonamide;
5-[4-(4-fluorophenyl)-1-(hydroxymethyl)cyclopenta-2,4-dien-3-yl]-2-pyridinesulfonamide;
5-[4-(4-fluorophenyl)-1-(methoxycarbonyl)cyclopenta-2,4-dien-3-yl]-2-pyridinesulfonamide;
5-[4-(4-fluorophenyl)-1-(trifluoromethyl)cyclopenta-2,4-dien-3-yl]-2-pyridinesulfonamide;
5-[4-(4-fluorophenyl)-1-carboxycyclopenta-2,4-dien-3-yl]-2-pyridinesulfonamide;
5-[4-(4-fluorophenyl)-1-(fluoromethyl)cyclopenta-2,4-dien-3-yl]-2-pyridinesulfonamide;
5-[4-(4-trifluoromethylphenyl)-1-methylcyclopenta-2,4-dien-3-yl]-2-pyridinesulfonamide;
5-[4-(4-trifluoromethylphenyl)-1-ethylcyclopenta-2,4-dien-3-yl]-2-pyridinesulfonamide;
5-[4-(4-trifluoromethylphenyl)-1-(hydroxymethyl) cyclopenta-2,4-dien-3-yl]-2-pyridinesulfonamide;
5-[4-(4-trifluoromethylphenyl)-1-(methoxycarbonyl)cyclopenta-2,4-dien-3-yl]-2-pyridinesulfonamide;
5-[4-(4-trifluoromethylphenyl)-1-(trifluoromethyl)cyclopenta-2,4-dien-3-yl]-2-pyridinesulfonamide;
5-[4-(4-trifluoromethylphenyl)-1-carboxycyclopenta-2,4-dien-3-yl]-2-pyridinesulfonamide;
5-[4-(4-trifluoromethylphenyl)-1-(fluoromethyl)cyclopenta-2,4-dien-3-yl]-2-pyridinesulfonamide;
5-[4-(4-fluorophenyl)-1,1-dimethylcyclopenta-2,4-dien-3-yl]-2-(methylsulfonyl)pyridine;
5-[4-(4-fluorophenyl)-1,1-diethylcyclopenta-2,4-dien-3-yl]-2-(methylsulfonyl)pyridine;
5-[4-(4-fluorophenyl)-1,1-bis(hydroxymethyl)cyclopenta-2,4-dien-3-yl]-2-(methylsulfonyl)pyridine;
5-[4-(4-fluorophenyl)-1,1-bis(methoxycarbonyl)cyclopenta- 2,4-dien-3-yl]-2-(methylsulfonyl)pyridine;

5-[4-(4-fluorophenyl)-1,1-bis(trifluoromethyl)cyclopenta-2,4-dien-3-yl]-2-(methylsulfonyl)pyridine;
5-[4-(4-fluorophenyl)-1,1-dicarboxycyclopenta-2,4-dien-3-yl]-2-(methylsulfonyl)pyridine;
5-[4-(4-fluorophenyl)-1,1-bis(fluoromethyl)cyclopenta-2,4-dien-3-yl]-2-(methylsulfonyl)pyridine;
5-[4-(4-trifluoromethylphenyl)-1,1-dimethylcyclopenta-2,4-dien-3-yl]-2-(methylsulfonyl)pyridine;
5-[4-(4-trifluoromethylphenyl)-1,1-diethylcyclopenta-2,4-dien-3-yl]-2-(methylsulfonyl)pyridine;
5-[4-(4-trifluoromethylphenyl)-1,1-bis(hydroxymethyl)-cyclopenta-2,4-dien-3-yl]-2-(methylsulfonyl)pyridine;
5-[4-(4-trifluoromethylphenyl)-1,1-bis (methoxycarbonyl)cyclopenta-2,4-dien-3-yl]-2-(methylsulfonyl)-pyridine;
5-[4-(4-trifluoromethylphenyl)-1,1-bis(trifluoromethyl)-cyclopenta-2,4-dien-3-yl]-2-(methylsulfonyl)pyridine;
5-[4-(4-trifluoromethylphenyl)-1,1-dicarboxycyclopenta-2,4-dien-3-yl]-2-(methylsulfonyl)pyridine;
5-[4-(4-trifluoromethylphenyl)-1,1-bis(fluoromethyl)cyclopenta-2,4-dien-3-yl]-2-(methylsulfonyl)pyridine;
5-[4-(4-fluorophenyl)-1,1-dimethylcyclopenta-2,4-dien-3-yl]-2-pyridinesulfonamide;
5-[4-(4-fluorophenyl)-1,1-diethylcyclopenta-2,4-dien-3-yl ]-2-pyridinesulfonamide;
5-[4-(4-fluorophenyl)-1,1-bis(hydroxymethyl)cyclopenta-2,4-dien-3-yl]-2-pyridinesulfonamide;
5-[4-(4-fluorophenyl)-1,1-bis(methoxycarbonyl)cyclopenta-2,4-dien-3-yl]-2-pyridinesulfonamide;
5-[4-(4-fluorophenyl)-1,1-bis(trifluoromethyl)cyclopenta-2,4-dien-3-yl]-2-pyridinesulfonamide;
5-[4-(4-fluorophenyl)-1,1-dicarboxycyclopenta-2,4-dien-3-yl ]-2-pyridinesulfonamide;
5-[4-(4-fluorophenyl)-1,1-bis(fluoromethyl)cyclopenta-2,4-dien-3-yl]-2-pyridinesulfonamide;
5-[4-(4-trifluoromethylphenyl)-1,1-dimethylcyclopenta-2,4-dien-3-yl]-2-pyridinesulfonamide;
5-[4-(4-trifluoromethylphenyl)-1,1-diethylcyclopenta-2,4-dien-3-yl]-2-pyridinesulfonamide;
5-[4-(4-trifluoromethylphenyl)-1,1-bis(hydroxymethyl)-cyclopenta-2,4-dien-3-yl]-2-pyridinesulfonamide;
5-[4-(4-trifluoromethylphenyl)-1,1-bis(methoxycarbonyl)cyclopenta-2,4-dien-3-yl]-2-pyridinesulfonamide;
5-[4-(4-trifluoromethylphenyl)-1,1-bis(trifluoromethyl)-cyclopenta-2,4-dien-3-yl]-2-pyridinesulfonamide;
5-[4-(4-trifluoromethylphenyl)-1,1-dicarboxycyclopenta-2,4-dien-3-yl]-2-pyridinesulfonamide;
5-[4-(4-trifluoromethylphenyl)-1,1-bis(fluoromethyl)cyclopenta-2,4-dien-3-yl]-2-pyridinesulfonamide;
1-methylsulfonyl-4-[1-methyl-1-trifluoromethyl-4-(4-methylphenyl)cyclopenta-2,4-dien-3-yl]benzene;
1-methylsulfonyl-4-[1-methyl-1-trifluoromethyl-4-(4-fluorophenyl)cyclopenta-2,4-dien-3-yl]benzene;
1-methylsulfonyl-4-[1-methyl-1-trifluoromethyl-4-(4-chlorophenyl)cyclopenta-2,4-dien-3-yl]benzene; and
1-methylsulfonyl-4-[1-methyl-1-trifluoromethyl-4-(4-trifluoromethylphenyl)cyclopenta-2,4-dien-3-yl]benzene.

Within Formula I there is a fourth subclass of compounds of high interest represented by Formula V:

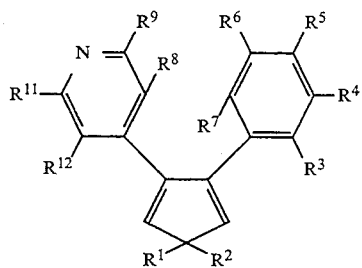

wherein each of $R^1$ and $R^2$ is independently selected from hydrido, alkyl, hydroxyalkyl, halo, haloalkyl, alkoxycarbonyl and carboxyl; and wherein each of $R^3$ through $R^9$, $R^{11}$ and $R^{12}$ is independently selected from hydrido, halo, alkyl, alkylthio, cyano, hydroxyl, mercapto, haloalkyl, alkoxy, haloalkoxy, hydroxyalkyl, alkoxyalkyl, alkylsulfonyl, haloalkylsulfonyl and sulfamyl;

or a pharmaceutically-acceptable salt or prodrug thereof.

A preferred class of compounds consists of those compounds of Formula V wherein each of $R^1$ and $R^2$ is independently selected from hydrido, lower alkyl, lower hydroxyalkyl, halo, lower haloalkyl, lower alkoxycarbonyl and carboxyl; and wherein each of $R^3$ through $R^9$, $R^{11}$ and $R^{12}$ is independently selected from hydrido, halo, lower alkyl, lower alkylthio, cyano, hydroxyl, mercapto, lower haloalkyl, lower alkoxy, lower haloalkoxy, lower hydroxyalkyl, lower alkoxyalkyl, lower alkylsulfonyl, lower haloalkylsulfonyl and sulfamyl.

A more preferred class of compounds consists of those compounds of Formula V wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^9$, $R^{11}$ and $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, hydroxyl, mercapto, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, trifluoromethylsulfonyl and sulfamyl.

A family of specific compounds of particular interest within Formula V consists of compounds and pharmaceutically-acceptable salts thereof as follows:
4-[4-[4-(methylsulfonyl)phenyl]cyclopenta-2,4-dien-3-yl]pyridine;

4-[4-(4-pyridyl)cyclopenta-2,4-dien-3-yl]benzenesulfonamide;
4-[4-[4-(methylsulfonyl)phenyl]1,1-dimethylcyclopenta-2,4-dien-3-yl]pyridine;
4-[4-[4-(methylsulfonyl)phenyl]1,1-diethylcyclopenta-2,4-dien-3-yl]pyridine;
4-[4-[4-(methylsulfonyl)phenyl]1,1-bis(hydroxymethyl)cyclopenta-2,4-dien-3-yl]pyridine;
4-[4-[4-(methylsulfonyl)phenyl]1,1-bis(methoxycarbonyl)cyclopenta-2,4-dien-3-yl]pyridine;
4-[4-[4-(methylsulfonyl)phenyl]1,1-difluorocyclopenta-2,4-dien-3-yl]pyridine;
4-[4-[4-(methylsulfonyl)phenyl]1,1-bis (trifluoromethyl)cyclopenta-2,4-dien-3-yl]pyridine;
4-[4-[4-(methylsulfonyl)phenyl]1,1-bis(fluoromethyl)cyclopenta-2,4-dien-3-yl]pyridine;
4-[4-(4-pyridyl)-1,1-dimethylcyclopenta-2,4-dien-3-yl]benzenesulfonamide;
4-[4-(4-pyridyl)-1,1-diethylcyclopenta-2,4-dien-3-yl]benzenesulfonamide;
4-[4-(4-pyridyl)-1,1-bis(hydroxymethyl)cyclopenta-2,4-dien-3-yl]benzenesulfonamide;
4-[4-(4-pyridyl)-1,1-bis(methoxycarbonyl)cyclopenta-2,4-dien-3-yl]benzenesulfonamide;
4-[4-(4-pyridyl)-1,1-difluorocyclopenta-2,4-dien-3-yl]benzenesulfonamide;
4-[4-(4-pyridyl)-1,1-bis(trifluoromethyl)cyclopenta-2,4-dien-3-yl]benzenesulfonamide; and
4-[4-(4-pyridyl)-1,1-bis(fluoromethyl)cyclopenta-2,4-dien-3-yl]benzenesulfonamide.

Where the term "alkyl" is used, either alone or within other terms such as "haloalkyl", "alkoxyalkyl" and "hydroxyalkyl", embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo and polyhaloalkyl radicals may have two or more of the same halo atoms or a combination of different halo radicals. The term "hydroxyalkyl" embraces linear or branched alkyl radicals having one to about twelve carbon atoms any one of which may be substituted with one or more hydroxyl radicals. The terms "alkoxy" and "alkoxyalkyl" embrace linear or branched oxy-containing radicals each having alkyl portions of one to about twelve carbon atoms, such as methoxy radical. The term "alkoxyalkyl" also embraces alkyl radicals having two or more alkoxy radicals attached to the alkyl radical, that is, to form monoalkoxyalkyl and dialkoxyalkyl radicals. The "alkoxy" or "alkoxyalkyl" radicals may be further substituted with one or more halo atoms, such as fluoro, chloro or bromo, to provide haloalkoxy or haloalkoxyalkyl radicals. The term "alkylthio" embraces radicals containing a linear or branched alkyl radical, of one to about twelve carbon atoms attached to a divalent sulfur atom, such as a methythio radical. The term "aryl" embraces aromatic radicals such as phenyl, naphthyl and biphenyl. Preferred aryl radicals are those consisting of one, two, or three benzene rings. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. The "alkylsulfonyl" radicals may be further substituted with one or more halo atoms, such as fluoro, chloro or bromo, to provide haloalkylsulfonyl radicals. The terms "sulfamyl" or "sulfonamidyl" denotes a sulfonyl radical substituted with an amine radical, forming a sulfonamide (—SO$_2$NH$_2$). The term "carboxyl", whether used alone or with other terms, denotes —CO$_2$H. The term "alkoxycarbonyl" means a radical containing an alkoxy radical, as defined above, attached via an oxygen atom to a "carbonyl" (—C=O) radical. Examples of such "alkoxycarbonyl" radicals include (CH$_3$)$_3$CO$_2$C— and —CO$_2$CH$_3$.

The present invention comprises a pharmaceutical composition for the treatment of inflammation and inflammation-associated disorders, such as arthritis, comprising a therapeutically-effective amount of a compound of Formula I in association with at least one pharmaceutically-acceptable carrier, adjuvant or diluent.

The present invention also comprises a therapeutic method of treating inflammation or inflammation-associated disorders in a subject, the method comprising administering to a subject having such inflammation or disorder a therapeutically-effective amount of a compound of Formula I.

Also included in the family of compounds of Formula I are isomeric forms including diastereoisomers, prodrugs and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I. The term "prodrug" embraces compounds which are metabolized in vivo into compounds of the invention.

GENERAL SYNTHETIC PROCEDURES

The compounds of the invention can be synthesized according to the following procedures of Schemes I-XV, wherein the R¹-R¹² substituents are as defined for Formula I, above, except where further noted.

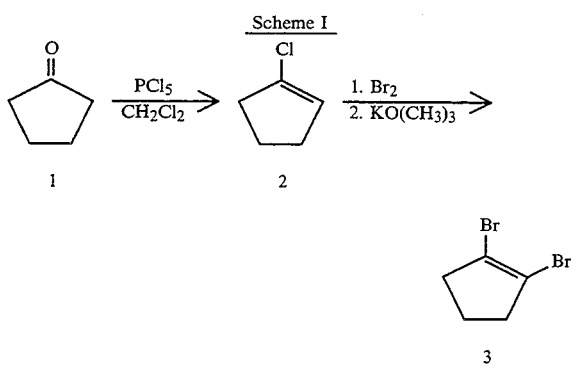

Synthetic Scheme I shows the preparation of 1,2-dibromocyclopentene (3) in two steps from commercially available cyclopentenone (1) using a procedure similar to the one developed by Montgomery et al. [J. Am. Chem. Soc., 87, 1917 (1965)]. In step one, chlorination with phosphorus pentachloride gives 1-chlorocyclopentene In step two, bromination of 2, followed by the elimination of hydrogen chloride on treatment with potassium tert-butoxide, provides 3.

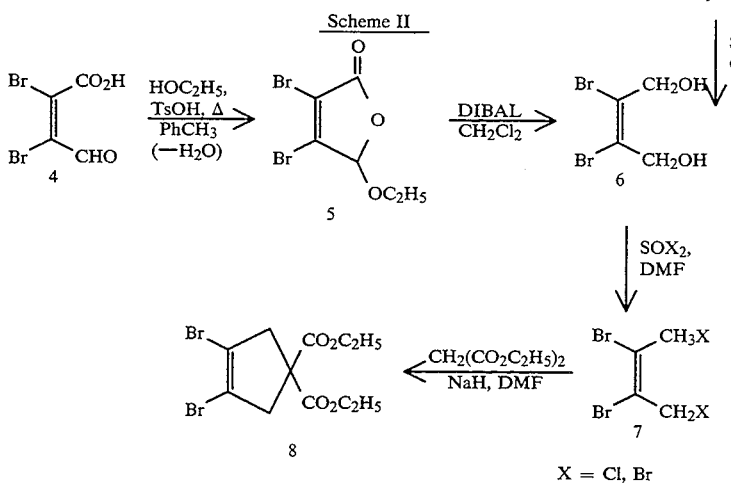

Synthetic Scheme II shows the preparation of 1,2-dibromo-4,4-dicarboethoxycyclopentene (8) in four steps from commercially available mucobromic acid (4) using a procedure similar to the one developed by Lerstrup et al. [Syn.Metals, 19, 647 (1987)]. In step one, mucobromic acid is converted to its ethyl ester 5 on treatment with ethanol in toluene at reflux in the presence of p-toluenesulfonic acid (TsOH). In step two, reduction of 5 with diisobutylaluminum hydride (DIBAL) in methylene chloride gives the diol 6. In step three, the diol 6 is reacted with thionyl chloride in dimethylformide (DMF) to give the corresponding 1,4-dichloride 7 (X=Cl). In step four, the 1,4-dihalo 7 is dialkylated with the dianion of diethyl malonate to give 8.

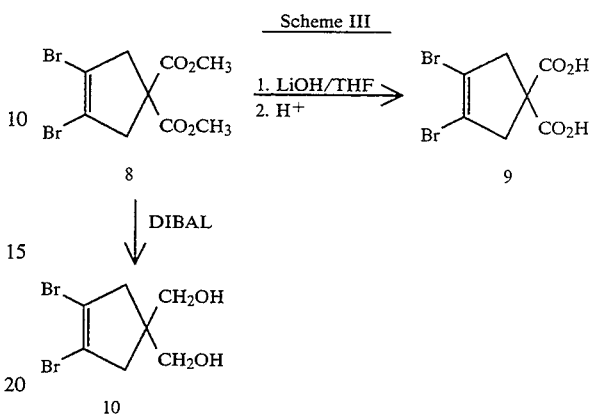

Synthetic Scheme III shows the preparation of 1,2-dibromo-4,4-dicarboxycyclopentene (9) and 1,2-bromo4,4-di(hydroxymethyl)cyclopentene (10) from synthetic intermediate 8 (prepared in Synthetic Scheme II). Reaction of 8 with lithium hydroxy in tetrahydrofuran (THF) followed by careful acidification at 0° C. gives the diacid 9; treatment with DIBAL gives the corresponding diol 10.

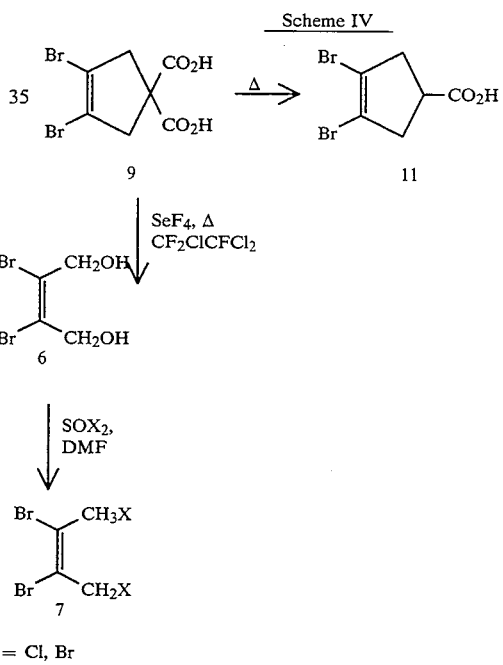

Scheme IV

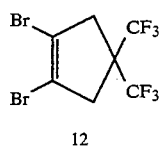
12

Synthetic Scheme IV shows the preparation of 1,2-dibromo-4-carboxycyclopentene (11) and 1,2-dibromo4,4-bistrifluoromethylcyclopentent (12) from synthetic intermediate 9 (prepared in Synthetic Scheme III). On heating, the diacid 9 is converted to the monoacid 10; treatment with selenium tetrafluoride in 1,1,2-trichlorotrifluoroethane at reflux gives the bistrifluoromethyl analog 12.

Scheme V

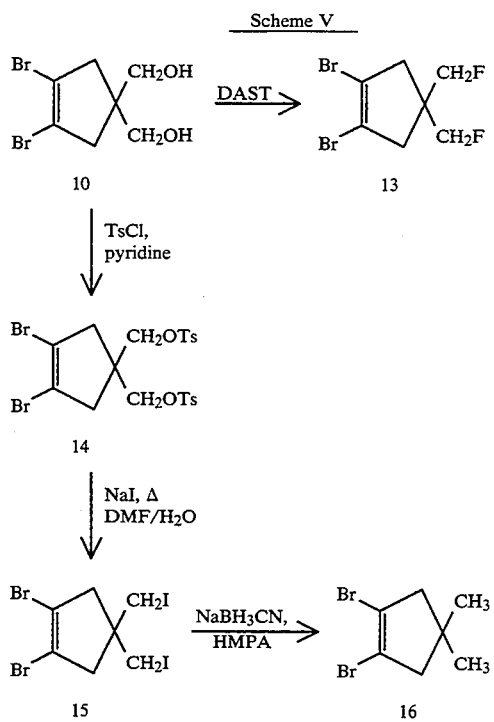

Synthetic Scheme V shows the preparation of 1,2-dibromo-4,4-bisfluoromethylcyclopentene (13) and 1,2-dibromo-4,4-dimethylcyclopentene (16) from synthetic intermediate 10 (prepared in Synthetic Scheme III). Treatment of the diol 10 with diethylaminosulfurtrifluoride (DAST) in methylene chloride gives the corresponding fluoromethyl analog 13. Reaction of 10 with p-toluenesulfonyl chloride (TsCl) in the presence of pyridine gives the ditosylate 14. Reaction of 14 with sodium iodide in DMF/water (3:1) at 150° C. gives the bisiodomethyl analog 15 which is subsequently reduced with sodium cyanoborohydride to give the dimethyl analog 16.

Scheme VI

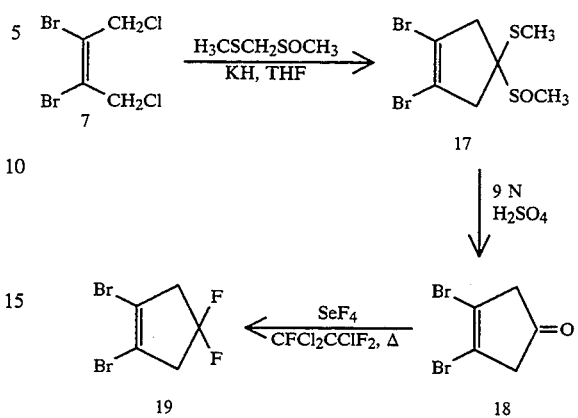

Synthetic Scheme VI shows the preparation of 1,2-dibromo-4,4-difluorocyclopentene (19) from synthetic intermediate 7 (prepared in Synthetic Scheme II). Using a procedure similar to the one developed by Ogura et al [Tertahedron Let., 32, 2767 (1975)], the dianion of methyl methylthiomethyl sulfoxide (generated by potassium hydride in THF) is reacted with 7 to give the dimethyl dithioacetal S-oxide 17. Subsequent hydrolysis with 9N sulfuric acid gives the corresponding ketone 18. Reaction of 18 with selenium tetrafluoride in 1,1,2-trichlorotrifluoroethane at reflux gives the 4,4-difluoro analog 19.

Scheme VII

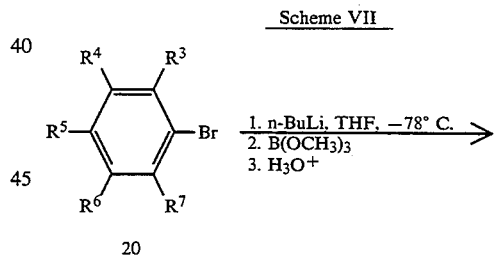

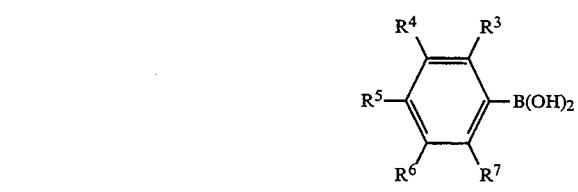

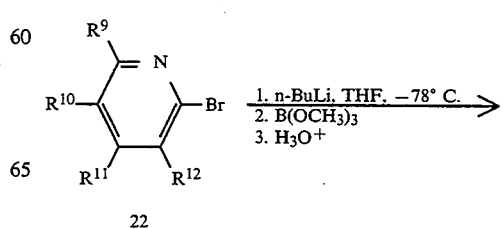

-continued
Scheme VII

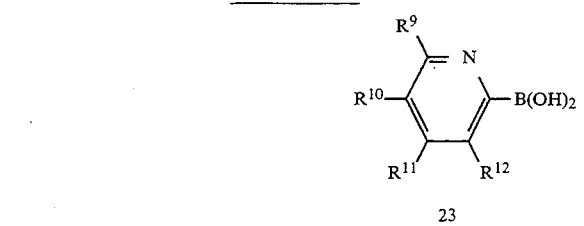

23

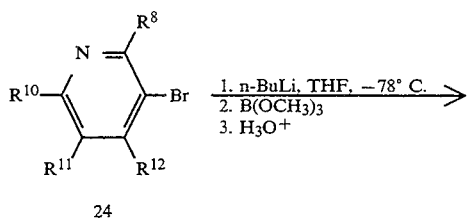

24

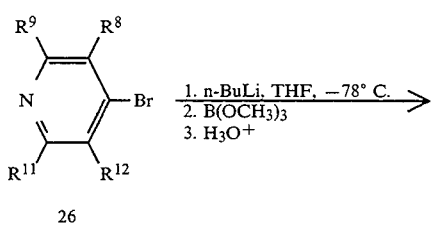

25

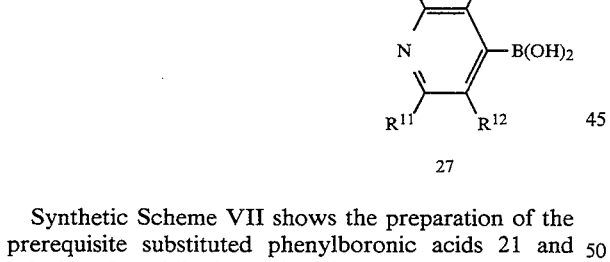

26

27

Synthetic Scheme VII shows the preparation of the prerequisite substituted phenylboronic acids 21 and substituted pyridinylboronic acids 23, 25, and 27 from the available bromides 20, 22, 24, and 26, respectively. Halogen-metal interchange in THF at −78° C. generates the corresponding organolithium reagents which are reacted with trimethyl borate. Hydrolysis with 3N hydrochloric acid provides the substituted phenylboronic acids 21 and the substituted pyridinylboronic acids 23, 25, and 27, respectively.

Scheme VIII

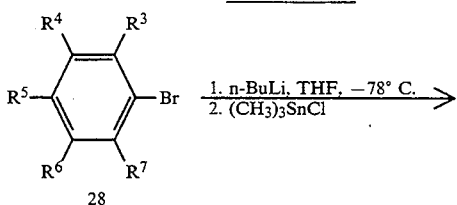

28

-continued
Scheme VIII

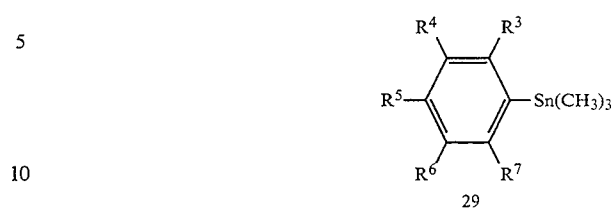

29

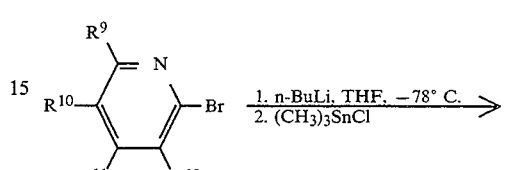

30

31

32

33

34

35

Synthetic Scheme VIII shows the preparation of the prerequisite substitutedphenyltrimethyltin analogs 29 and substitutedpyridinyltrimethyltin analogs 31, 33, and from the available bromides 28, 30, 32, and 34, respectively. Halogen-metal interchange in THF at −78° C.

generates the organolithium reagents which are reacted with trimethyltin chloride. Purification provides the substitutedphenyltrimethyltin analogs 29 and the substitutedpyridinyltrimethyltin analogs 31, 33, and 35, respectively.

pared in Synthetic Scheme I-VI) in the presence of Pd° catalyst, e.g., tetrakis(triphenylphosphine)-palladium (0), to give the monocoupled bromides 38 (after separation from the biscoupled by-produce). In step three, the bromides 38 are treated as above to give the organozinc

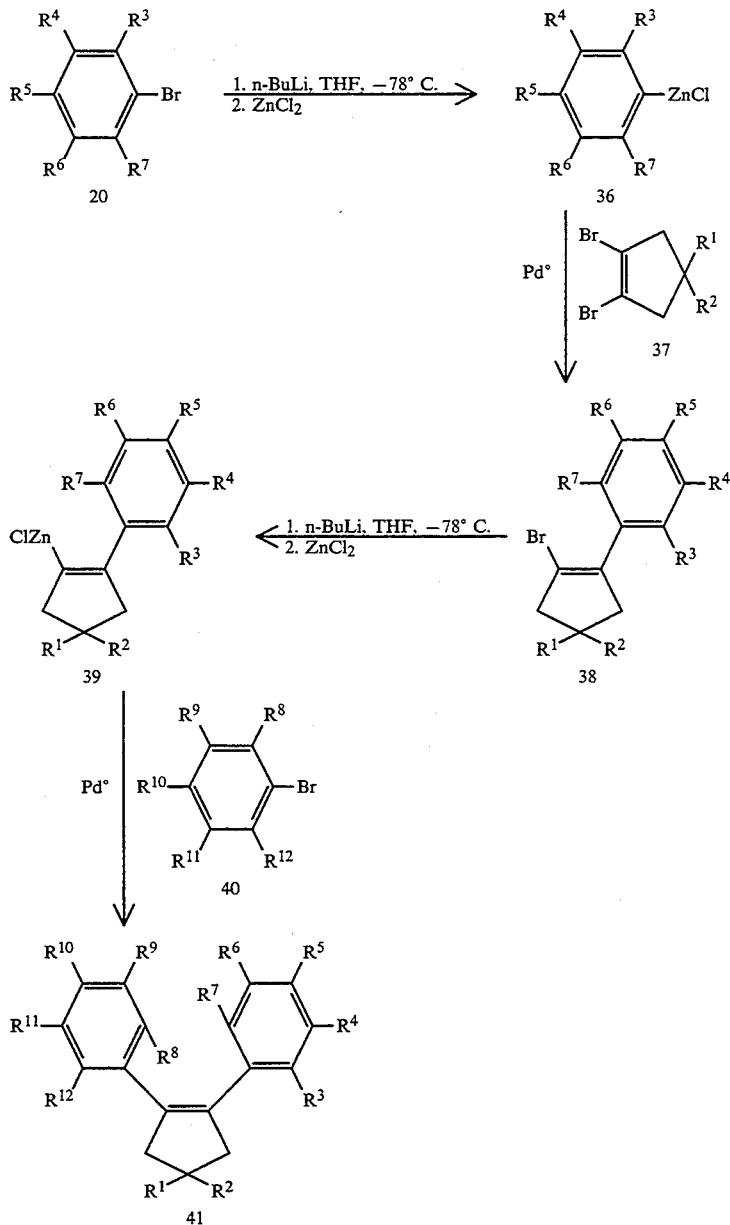

Synthetic Scheme IX shows the five step procedure for the preparation of 3,4-diaryl-1,1-disubstitutedcyclopenta-2,4-diene antiinflammatory agents from the available bromides 20 using a sequential coupling procedure which is similar to the coupling procedure developed by Negishi et al. [J. Org. Chem., 42, (1977)]. In step one, halogen-metal interchange of with n-butyllithium in THF at 78° C. gives the corresponding organolithium reagents which subsequently react with zinc chloride to give the organozinc reagents 36. In step two, the organozinc reagents 36 are coupled with the 1,2-dibromo-4,4-disubstitutedcyclopentenes 37 (prereagents 39. In step four, the monocoupled organozinc reagents 39 are coupled with the arylbromides 40 (which can be identical with 20 when $R^3=R^8$, $R^4=R^9$, $R^5=R^{10}$, $R^6=R^{11}$ and $R^7=R^{12}$) to give the 1,2-diaryl-4,4-disubstitutedcyctopentenes 41. In step give, the cyclopentene analogs 41 are first reacted with m-chloroperoxybenzoic acid (MCPBA) in methylene chloride at ambient temperature to give the corresponding epoxides which are subsequently reacted with sodium acetate in acetic acid/water (9:1) at 80° C. to give the 3,4-diaryl1,1-disubstitutedcyclopententa-2,4-diene anti-inflammatory agents 42 of this invention Scheme X

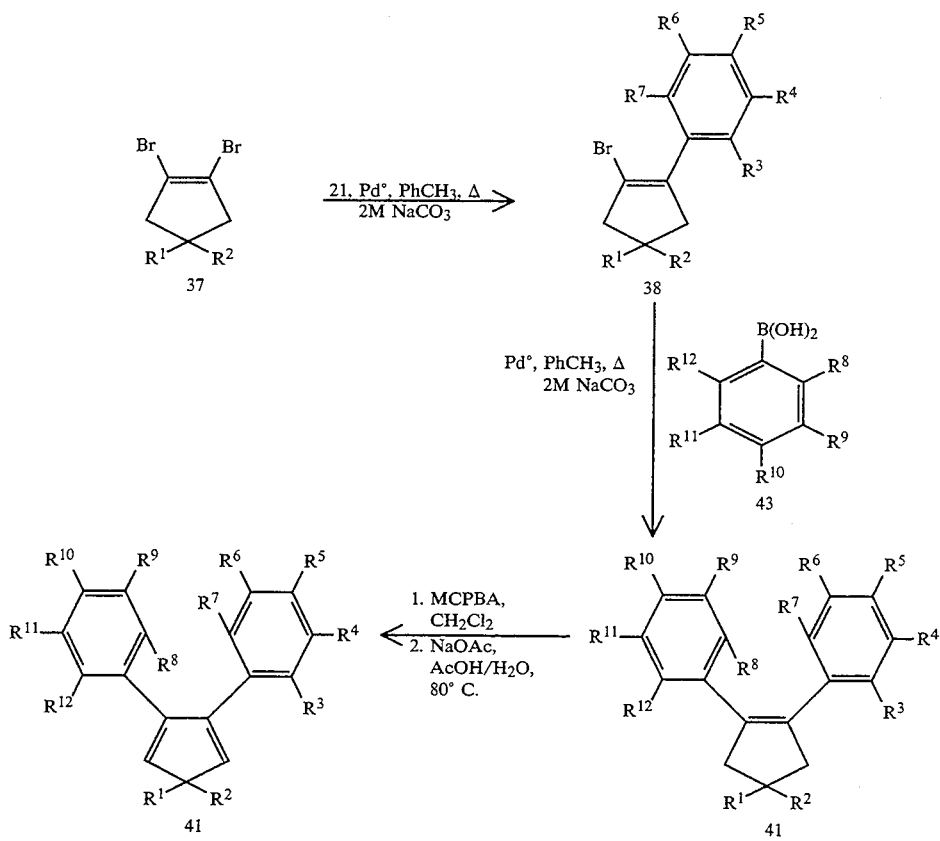

Synthetic Scheme X shows the three step procedure for the preparation of 3,4-diaryl-1,1-disubstitutedcyclopenta-2,4-diene antiinflammatory agents from 1,2-dibromo-4,4-disubstitutedcyclopentenes 37 (prepared in Synthetic Scheme I-VI) and substituted phenylboronic acids 21 and 43 (prepared in Synthetic Scheme VII) using a sequential coupling procedure which is similar to the coupling procedure developed by Suzuki et al. [Syn. Commun., 11, 513 (1981)]. In step one, the dibromides 37 are treated with the boronic acids 21 in toluene at reflux in the presence of a Pd° catalyst, e.g., tetrakis(-triphenylphosphine-palladium (0), and 2M sodium carbonate to give the monocoupled bromides 38 (after separation from the biscoupled by-product). In step two, the monocoupled bromides 38 are coupled as above with the boronic acids 43 (which can be identical with 21 when $R^3=R^8$, $R^4=R^9$, $R^5=R^{10}$, $R^6=R^{11}$ and $R^7=R^{12}$) to give the 12-diaryl-4,4-disubstitutedcyclopentenes 41. In step three, the cyclopentene analogs 41 are first reacted with m-chloroperoxybenzoic acid (MCPBA) in methylene chloride at ambient temperature to give the corresponding epoxides which are subsequently reacted with sodium acetate in acetic acid/water (9:1) at 80° C. to give the 3,4-diaryl-1,1-disubstitutedcyclopenta-2,4-diene anti-inflammatory agents 42 of this invention.

Scheme XI

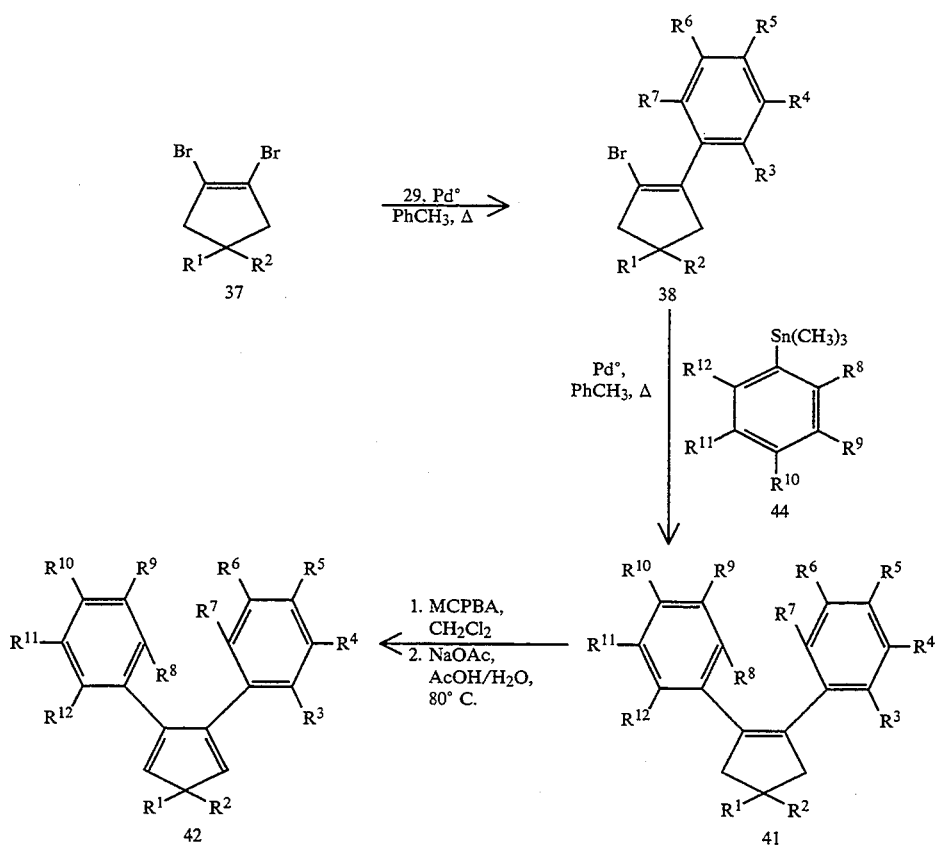

Synthetic Scheme XI shows the three step procedure for the preparation of 3,4-diaryl-1,1-disubstitutedcyclopenta-2,4-diene antiinflammatory agents from 1,2-dibromo-4,4-disubstitutedcyclopentenes 37 (prepared in Synthetic Scheme I–VI) and substitutedphenyltrimethyltin analogs 29 and 43 (prepared in Synthetic Scheme VII) using a sequential coupling procedure which is similar to the coupling procedure developed by Stille et al. [J. Am. Chem. Soc., 101, 4992 (1979)]. In step one, the dibromides 37 are treated with the trimethyltin analogs 29 in toluene at reflux in the presence of a Pd° catalyst, e.g., tetrakis(triphenylphosphine)palladium (0), and 2M sodium carbonate to give the monocoupled bromides 38 (after separation from the biscoupled by-product). In step two, the monocoupled bromides 38 are coupled as above with the trimethyl analogs 44 (which can be identical with 29 when $R^3=R^8$, $R^4=R^9$, $R^5=R^{10}$, $R^6=R^{11}$ and $R^7=R^{12}$) to give the 1,2-diaryl-4,4-disubstitutedcyclopentenes of 41. In step three, the cyclopentene analogs 41 are first reacted with m-chloroperoxybenzoic acid (MCPBA) in methylene chloride at ambient temperature to give the corresponding epoxides which are subsequently reacted with sodium acetate in acetic acid/water (9:1) at 80° C. to give the 3,4-diaryl1,1-disubstitutedcyclopenta-2,4-diene antiinflammatory agents 42 of this invention.

Scheme XII

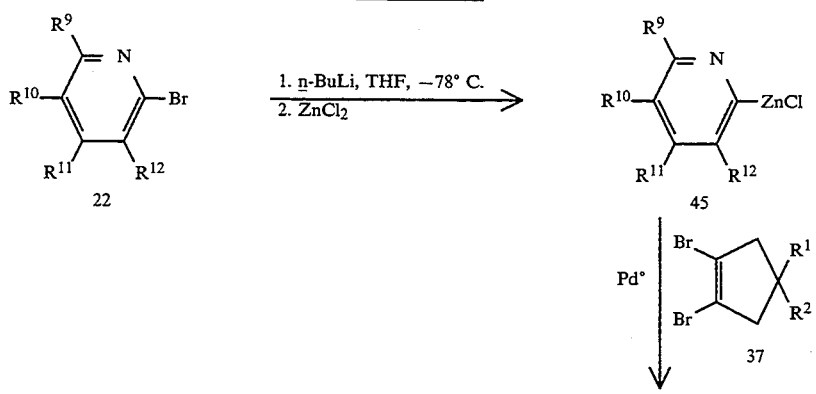

Scheme XII

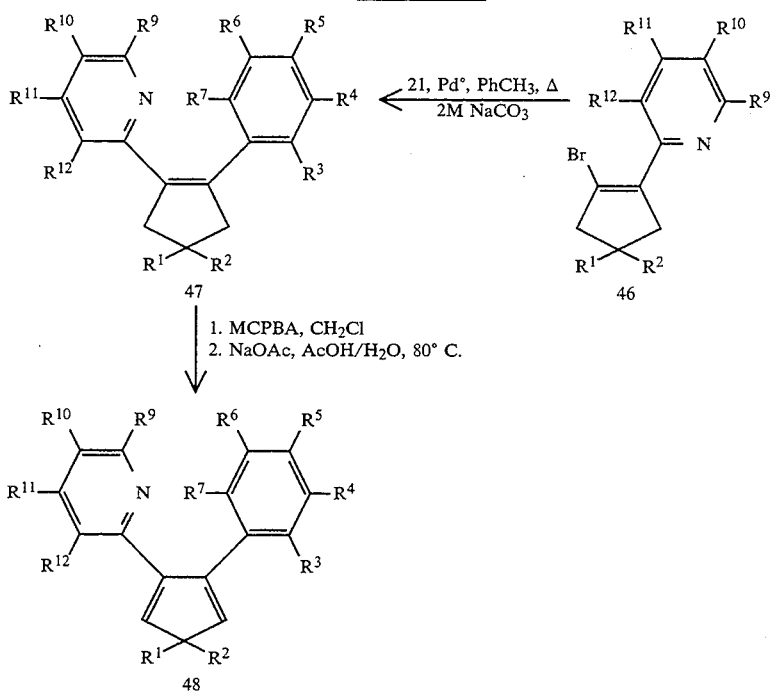

Synthetic Scheme XII shows the four step preparation of 3-aryl-4-(2-pyridinyl)-1,1-disubstitutedcyclopentadiene antiinflammatory agents 48 from 1,2-dibromo-4,4-disubstitutedcyclopentenes 37 (prepared in Synthetic Scheme I-VI) and the available 2-bromopyridines 22. In step one, halogen-metal interchange of 22 with n-butyllithium in THF at −78° C. gives the 2-lithiopyridines which subsequently react with zinc chloride to give the corresponding 2-pyridinylzinc reagents 44. In step two, a Negishi coupling (see Synthetic Scheme IX) of the 2-pyridinylzinc reagents 45 with 37 gives the monocoupled 2-pyridinyl bromides 46 (after separation from the biscoupled by-product). In step three, a Suzuki coupling (see Synthetic Scheme X) of the monocoupled 2-pyridinyl bromides 46 with substituted phenylboronic acids 21 (prepared in Synthetic Scheme VII) gives the 3-aryl-4-(2-pyridinyl)-1,1-disubstitutedcyclopentenes 47. In step four, the cyclopentene analogs 47 are first reacted with m-chloroperoxybenzoic acid (MCPBA) in methylene chloride at ambient temperature to give the corresponding epoxides which are subsequently reacted with sodium acetate in acetic acid/water (9:1) at 80° C. to give the 3-aryl-4-(2-pyridinyl)-1,1-disubstitutedcyclopentadiene antiinflammatory agents 48 of this invention.

Scheme XIII

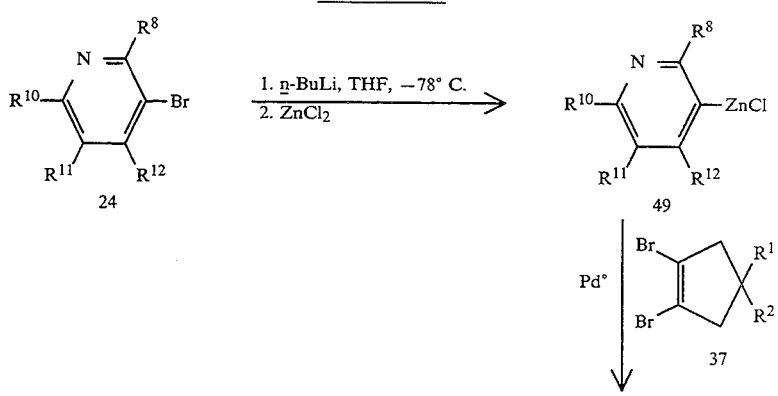

Scheme XIII

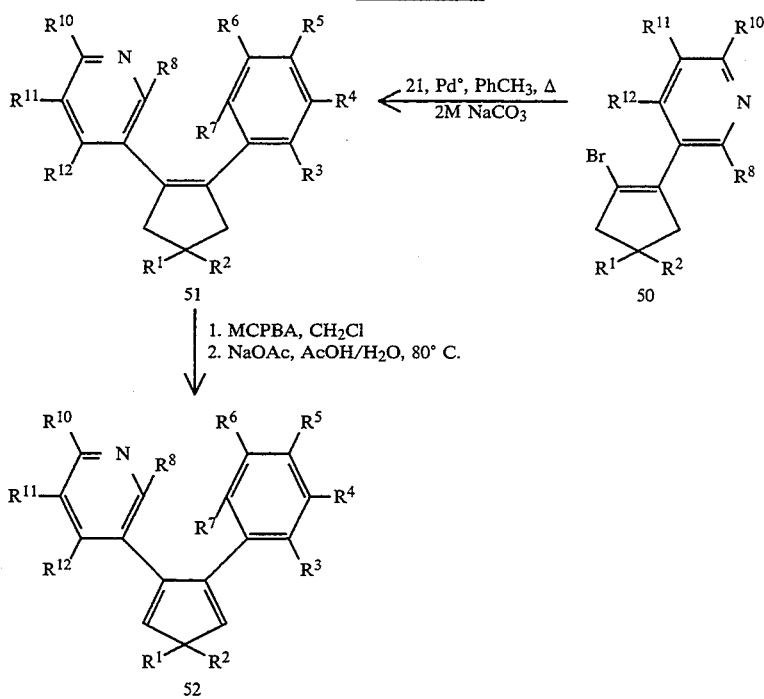

Synthetic Scheme XIII shows the four step preparation of 1-aryl-2-(3-pyridinyl)-4,4-disubstitutedcyclopentadiene antiinflammatory agents 52 from 1,2-dibromo-4,4-disubstitutedcyclopentenes 37 (prepared in Synthetic Scheme I-VI) and the available 3-bromopyridines 24. In step one, halogen-metal interchange of 24 with n-butyllithium in THF at −78° C. gives the 3-lithiopyridines which subsequently react with zinc chloride to give the corresponding 3-pyridinylzinc reagents 49. In step two, a Negishi coupling (see Synthetic Scheme IX) of the 3-pyridinylzinc reagents 49 with 37 gives the monocoupled 3-pyridinyl bromides 50 (after separation from the biscoupled by-product). In step three, a Suzuki coupling (see Synthetic Scheme X) of the monocoupled 2-pyridinyl bromides 50 with substituted phenylboronic acids 21 (prepared in Synthetic Scheme VII) gives the 3-aryl-4-(3-pyridinyl)-1,1-disubstitutedcyclopentadienes 51. In step four, the cyclopentene analogs 51 are first reacted with m-chloroperoxybenzoic acid (MCPBA) in methylene chloride at ambient temperature to give the corresponding epoxides which are subsequently reacted with sodium acetate in acetic acid/water (9:1) at 80° C. to give the 3-aryl-4-(3-pyridinyl)-1,1-disubstitutedcyclopentadiene antiinflammatory agents 52 of this invention.

Scheme XIV

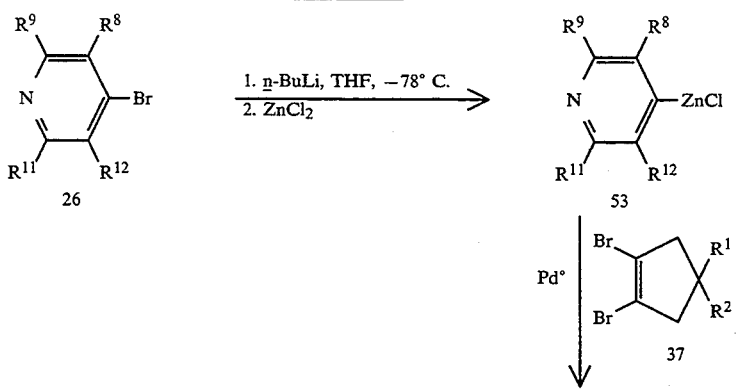

Scheme XIV

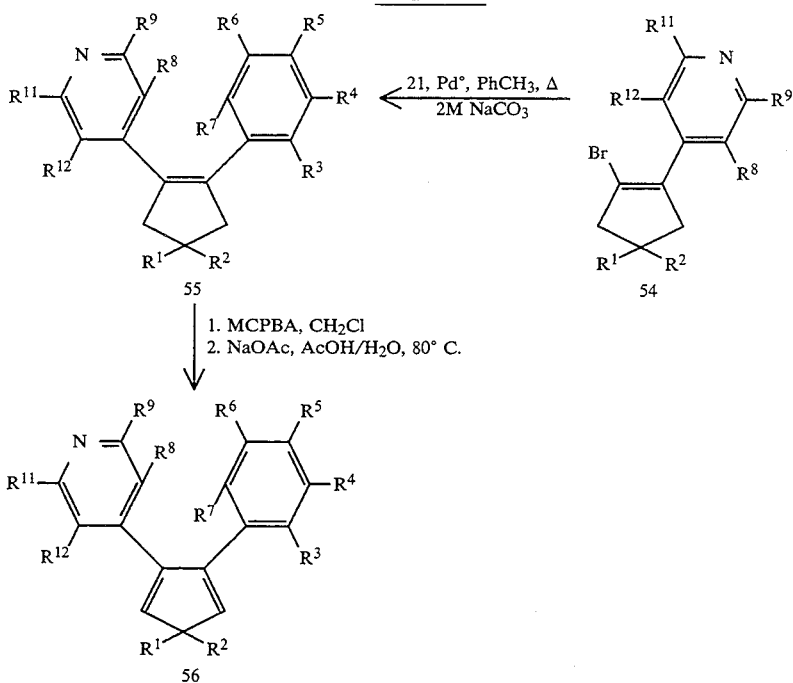

Synthetic Scheme XIV shows the four step preparation of 3-aryl-4-(4-pyridinyl)-1,1-disubstitutedcyclopentadiene antiinflammatory agents 56 from 1,2-dibromo-4,4-disubstitutedcyclopentenes 37 (prepared in Synthetic Scheme I-VI) and the available 4bromopyridines 26. In step one, halogen-metal interchange of 26 with n-butyllithium in THF at −78° C. gives the 4-lithiopyridines which subsequently react with zinc chloride to give the corresponding 4-pyridinylzinc reagents 53. In step two, a Negishi coupling (see Synthetic Scheme IX) of the 4-pyridinylzinc reagents 53 with 37 gives the monocoupled 4-pyridinyl bromides 54 (after separation from the biscoupled by-product). In step three, a Suzuki coupling (see Synthetic Scheme X) of the monocoupled 4-pyridinyl bromides 54 with substituted phenylboronic acids 21 (prepared in Synthetic Scheme VII) gives the 1-aryl-2-(4-pyridinyl)-1,1-disubstitutedcyclopentadienes 55. In step four, the cyclopentene analogs 55 are first reacted with m-chloroperoxybenzoic acid (MCPBA) in methylene chloride at ambient temperature to give the corresponding epoxides which are subsequently reacted with sodium acetate in acetic acid/water (9:1) at 80° C. to give the 3-aryl-4-(4-pyridinyl)-1,1-disubstitutedcyclopentadiene antiinflammatory agents 56 of this invention.

Scheme XV

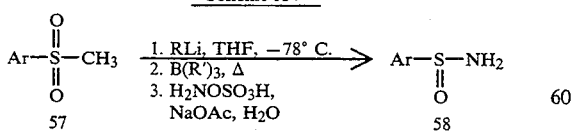

Synthetic Scheme XV shows the three step procedure used to prepare sulfonamide antiinflammatory agents 58 from their corresponding methyl sulfones 57. In step one, a THF solution of the methyl sulfones 57 at −78° C. are treated with an alkyllithium reagent, e.g., methyllithium, n-butyllithium, etc. In step two, the anions generated in step one is treated with an organoborane, e.g., triethylborane, tributylborane, etc., at −78° C. then allowed to warm to ambient temperature prior to stirring at reflux. In step three, an aqueous solution of sodium acetate and hydroxyamine-O-sulfonic acid is added to provide the corresponding sulfonamide antiinflammatory agents 58 of this invention.

The following examples contain detailed descriptions of the methods of preparation of compounds of Formula I-V. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

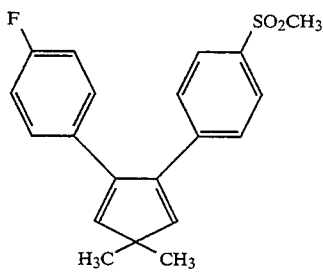

1-Methylsulfonyl-4-[1,1-dimethyl-4-(4-fluorophenyl)cyclopenta-2,4-dien-3-yl]benzene Step 1: Preparation of the ethyl acetal of mucobromic acid, Under nitrogen, a stirred solution of 500 g (1.94 mol) of mucobromic acid (Lancaster) and 2 g of p-toluenesulfonic acid monohydrate in 600 mL of toluene and mL of absolute ethanol was heated to reflux for 6 hours during which time 150 mL of a water, toluene, and ethanol azetrope was removed by distillation. The solution was concentrated in vacuo; the residue was dissolved in 1500 mL of ethyl acetate and washed with water, saturated sodium carbonate, and brine, dried ($Na_2SO_4$), and reconcentrated to give 440 g (79%) of the ethyl acetal of mucobromic acid (5 in Synthetic Scheme II) as an oil: NMR ($CDCl_3$) $\delta1.31$ (t, J=7 Hz, 3H), 3.73–3.96 (m, 2H), 5.81 (s, 1H).

Step 2: Preparation of cis-2,3-dibromobut-2-ene-1,4-diol

Under nitrogen, a stirred solution of 150 g (525 mmol) of the ethyl acetal of mucobromic acid (Step 1) in 150 mL of anhydrous THF at −78° C. was treated with 1400 mL of diisobutylaluminum hydride (1.5 M in toluene) over a 30 minute period. The solution was allowed to warm to ambient temperature and stirred for 2 hours. The reaction was slowly treated (maintaining the temperature below 10° C.) with 100 mL of acetone followed by 50 mL of 2.5 N sodium hydroxide. Water (1000 mL) was added and the solution extracted 5 times with ethyl acetate. The combined extracts were washed with brine, dried ($Na_2SO_4$), and concentrated. The residue was washed 3 times with hexane and dried in vacuo to give 88.5 g (69%) of cis-2,3-dibromo-2-ene-1,4-diol (6 in Synthetic Scheme II) as a colorless solid: mp 66°–67° C.; NMR (DMSO-$d_6$) $\delta4.27$ (d, J=6 Hz, 4H), 5.44 (t, J=6 Hz, 2H).

Step 3; Preparation of cis-1, 2,3,4-tetrabromobut-2-ene

Under nitrogen, a stirred solution of 25.2 g (102 mmol) of cis-2,3-dibromobut-2-ene-l,4-diol (Step 2) in 150 mL of methylene chloride at 0° C. was treated with 9.6 mL of phosphorus tribromide. The solution was allowed to warm to ambient temperature where it was allowed to stir for 1 hour prior to the addition of ice water. The aqueous phase was extracted 5 times with methylene chloride. These extracts were combined with the original methylene chloride phase and washed with water, saturated sodium carbonate, brine, dried ($Na_2SO_4$), and concentrated in vacuo to give 18 g (47%) of cis-1,2,3,4-tetrabromobut- 2-ene [7 (X=Br) in Synthetic Scheme II]as an oil: NMR ($CDCl_3$) $\delta4.40$ (s, 4H).

Step 4: Preparation of 1,2-dibromo-4,4-di(carboethoxy)cyclopentene

Under nitrogen, a solution of 9.7 g (60.6 mmol) of diethyl malonate in anhydrous THF at −10° C. was treated with 2.9 g (121 mmol) of sodium hydride (95%) and allowed to stir for 30 minutes. The resulting solution was then added slowly to 15 g (40.4 mmol) of cis-1,2,3,4-tetrabromobut-2-ene (Step 3) in 350 mL of anhydrous THF at −78° C. The reaction was allowed to warm to ambient temperature overnight prior to concentration in vacuo. The residue was dissolved in ethyl acetate and washed with water, dried ($Na_2SO_4$), and reconcentrated. Purification by silica gel chromatography (Waters Prep-500) with ethyl acetate/hexane (1:99) gave 3.7 g (25%) of 1,2,-dibromo-4,4-di(carboethoxy)-cyclopentene (8 in Synthetic Scheme II) as a colorless oil: NMR ($CDCl_3$) $\delta1.26$ (t, J=7 Hz, 6H), 3.26 (s, 4H), 4.22 (m, J=7 Hz, 4H); MS (FAB) for M+H m/e: 373, 371, 369.

Step 5: Preparation of 1,2-dibromo-4,4-di(hydroxymethyl)cyclopentene

Under nitrogen, a stirred solution of 8.7 g (23.5 mmol) of 1,2-dibromo-4,4-di(carboethoxy)cyclopentene (Step 4) in 70 mL of anhydrous THF at −78° C. was treated with 80 mL of diisobutylaluminum hydride (1.5 M in toluene) over a 20 minute period. The reaction was allowed to warm to ambient temperature overnight and was slowly treated with 20 mL of acetone followed by 10 mL of 2.5 N sodium hydroxide. Water (100 mL) was added and the solution extracted 5 times with ethyl acetate. The combined extracts were washed with brine, dried ($Na_2SO_4$), and concentrated in vacuo to give 5.7 g (85%) of 1,2-dibromo- 4,4-di (hydroxymethyl)cyclopentene (10 in Synthetic Scheme III) as a colorless oil: NMR ($CDCl_1$) $\delta2.20$ (s, 2H), 2.50 (s, 4H), 3.70 (s, 4H).

Step 6: Preparation of 1,2-dibromo-4,4-di(iodomethyl)cyclopentene

Under nitrogen, a stirred solution of 5.7 g (19.9 mmol) of 1,2-dibromo-4,4-di(hydroxymethyl)cyclopentene (Step 5) in 50 mL of pyridine at ambient temperature was treated with 19 g (99.7 mmol) of p-toluenesulfonyl chloride. The reaction was allowed to stir overnight and was concentrated in vacuo. The residue was dissolved ethyl acetate and washed twice with 3% hydrochloric acid followed by brine. The solution was dried ($Na_2SO_4$) and concentrated in vacuo to give 5.2 g (44%) of 1,2-dibromo-4,4-di(tosylmethyl)cyclopentene (14 in Synthetic Scheme V) as a colorless semisolid: NMR ($CDCl_3$) $\delta2.42$ (s, 4H), 2.47 (s, 6H), 3.90 (s, 4H), 7.37 (d, J=8 Hz, 4H), 7.74 (d, J=8 Hz, 4H).

Step 7: Preparation of 1,2-dibromo-4,4-di(iodomethyl)cyclopentene

Under nitrogen, a stirred solution of 5.2 g (8.7 mmol) of 1,2-dibromo-4,4-di(tosylmethyl)cyclopentene (Step 6) and 13 g (86 mmol) of sodium iodide in 40 mL of DMF/H2O (3:1) was heated to 150° C. in an oil bath overnight. The reaction was cooled, diluted with 200 mL of ethyl acetate, and washed with water. Drying ($Na_2SO_4$) and concentating in vacuo gave 3.7 g (84% ) of 1,2-dibromo-4,4-di (iodomethyl)cyclopentene (15 in Synthetic Scheme V) as an oil: NMR ($CDCl_3$) $\delta2.70$ (s, 4H), 3.50 (s, 4H).

Step 8: Preparation of 1,2-dibromo-4,4-dimethylcyclopentene

Under nitrogen, a stirred solution of 3.7 g (7.3 mmol) of 1,2-dibromo-4,4-di(iodomethyl)cyclopentene (Step 7) and 1.3 g (20.6 mmol) of sodium cyanoborohydride in 15 mL of hexamethylphosphoramide (HMPA) was heated to 100° C. in an oil bath overnight. The reaction was cooled, diluted with 50 mL of water, and extracted 5 times with ethyl acetate/hexane (1:5). The combined extracts were washed 3 times with water, dried ($Na_2SO_4$), and concentrated in vacuo. Purification by silica gel chromatography (Waters Prep-500) with hexane gave 1.3 g (70%) of 1,2-dibromo-4,4-dimethylcyclopentene (16 in Synthetic Scheme V) as a colorless oil: NMR ($CDCl_3$) $\delta1.16$ (s, 6H), 2.44 (s, 4H); MS (EI) m/e (rel intensity) 256 (24), 254 (63), 252(44), 175 (26), 173 (29), 94 (100).

Step 9 Preparation of 1-[2-(4-fluorophenyl)-4,4-dimethylcyclomenten-yl]-4-(methylthio)benzene, Under nitrogen, 1.3 g (5.1 mmol) of 1,2-dibromo-4,4-dimethylcyclopentene (Step 8) was reacted with 600 mg (4.3 mmol) of 4-fluorophenylboronic acid (Lancaster) in 23 mL of toluene, 15 mL of ethanol, and 10 mL of 2M $Na_2CO_3$ in the presence of 250 mg (5 mol %) of $Pd(PPh_3)_4$. The reaction was vigorously stirred at reflux overnight and concentrated in vacuo. The residue was dissolved in ethyl acetate and washed with water, dried ($Na_2SO_4$), and reconcentrated. Purification by silica gel chromatography (MPLC) with hexane gave 250 mg of 1-(2-bromocyclopenten-1-yl)-4-fluorobenzene (38 in Synthetic Scheme X when $R^1$ and $R^2=CH_3$, $R^5=F$, and $R^3$, $R^4$, $R^6$ and $R^7=H$) as a pale yellow oil which was reacted with 200 mg (1.2 mmol) of 4-methylthiophenylboronic acid (Example 1, Step 1) in 5.2 mL of toluene, 3.4 mL of ethanol, and 2.2 mL of 2H $Na_2CO_3$ in the presence of 40 mg (5 mol %) of $Pd(PPh_3)_4$. The reaction was vigorously stirred at reflux for 6 hours and concentrated in vacuo. The residue was dissolved in ethyl acetate and washed with water, dried ($Na_2SO_4$), and reconcentrated. Purification by silica gel chromatography (MPLC) with hexane gave 120 mg of 1-[2-(4-fluorophenyl)-4,4-dimethylcyclopenten-1-]-4-(methylthio)benzene (41 in Synthetic Scheme X when $R^1$ and $R^2=CH_3$, $RS=F$, $R^{10}=SCH_3$, and $R^3$, $R^4$, $R^6$, $R^7$, $R^8$, $R^9$, $R^{11}$, and $R^{12}=H$) as an oil: NMR $CDCl_3$) δ1.20 (s, 6H0, 2.42 (s, 3H), 2.63 (s, 4H), 6.90 (t, J=8 Hz, 2H), 7.00–7.18 (m, 4H), 7.30–7.60 (m, 2H).

Step 10; Preparation of 1-[2-(4-fluorophenyl)-4,4-dimethylcyclopenten-1-yl]-4-(methylsulfonyl) benzene.

A solution of 120 mg (0.39 mmol) of 1-[2-(4-fluorophenyl)-4,4-dimethylcyclopenten-1-yl]-4-(methylthio)-benzene (Step 9) in 3 mL of methanol/water (1:1) was slowly treated with 470 mg (0.76 mmol) of Oxone® [2 $KHSO_5 \cdot KHSO_4 \cdot K_2SO_4$] in 2 mL of water. After stirring for 4 hours, the solvent was removed in vacuo. The residue was dissolved in ethyl acetate and washed with water and brine, dried ($MgSO_4$), and reconcentrated. Purification by silica gel chromatography (MPLC) with hexane/ethyl acetate (5:1) and subsequent lyophilization from acetonitrile/water (1:1) gave 50 mg (38%) of 1-[2-(4-fluorophenyl)-4,4-dimethyl cyclopenten-1-yl]-4-(methylsulfonyl)benzene (41 in Synthetic Scheme X when $R^1$ and $R^2=CH_3$, $RS=F$, $R^{10}=SO_2CH_3$, and $R^3$, $R^4$, $R^6$, $R^7$, $R^8$, $R^9$, $R^{11}$ and $R12=H$) as a colorless solid: NMR ($CDCl_3$) δ1.24 (s, 6H), 2.71 (s, 4H), 3.4 (s, 3H), 6.92 (t, J=8 Hz, 2H), 7.05–7.12 (m, 2H), 7.30 (d, J=9 Hz, 2H), 7.75 (d, J=9 Hz, 3H); MS (EI) m/e (rel intensity) 344 (100), 329 (33), 250 (18), 235 (20), 109 (35), 69 (44); HRMS. Calc'd for $C_{20}H_{21}FO_2S$: 344.1246. Found: 344.1272.

Step 11; Preparation of 1-methylsulfonyl-4-[1,1-dimethyl-4-(fluorophenyl)cyclopenta-2,4-dien-3-yl]benzene, A solution of 196 mg (0.57 mmol) of 1-[2-(4-fluorophenyl)-4,4-dimethyl cyclopenten-1-yl]-4 -(methylsulfonyl) benzene (from Step 10) in 4 mL of dichloromethane was treated with 270 mg (55% peroxyacid, 0.86 mmol) of m-chloroperoxybenzoic acid (MCPBA). The reaction was stirred at ambient temperature for 5 hours, washed with aqueous saturated sodium bisulfite, dried ($MgSO_4$), and concentrated in vacuo to give a mixture of desired expoxide intermediate and m-chlorobenzoic acid; this crude mixture in 6 mL of acetic acid and 0.6 mL of water was subsequently treated with 300 mg (3.7 mmol) of sodium acetate and stirred at 80° C. for 10 hours. The reaction mixture was cooled to ambient temperature and concentrated in vacuo. The residue was partitioned between water and ethyl acetate; the organic phase was washed with aqueous saturated sodiun bicarbonate, water, brine, dried ($MgSO_4$), and reconcentrated in vacuo. Purification by silica gel chromatography gave 180 mg (92%) of 1-methylsulfonyl-4-[1,1-dimethyl-(4-fluorophenyl)cyclopenta-2,4-dien-3-yl]benzene (42 in Synthetic Scheme X when $R^1$ and $R^2=CH_3$, $R^5=F$, $R^{10}=SO_2CH_3$, and $R^3$, $R^4$, $R^6$, $R^7$, $R^8$, $R^9$, $R^{11}$ and $R^{12}=H$) as a colorless solid: mp 150°–152° C. (dec); NMR ($CDCl_3$) δ1.33 (s, 6H), 3.05 (s, 3H), 6.35 (d, J =2 Hz, 1H), 6.47 (d, J=2 Hz, 1H), 6.94 (t, J =9 Hz, 2H), 7.00–7.20 (m, 2H), 7.30 (dd, J=7 and 2 Hz, 2H), 7.80 (dd, J=7 and 2 Hz. HRMS (EI). Calc'd for M+Li: 349.1250. Found: 349.1257.

EXAMPLE 2

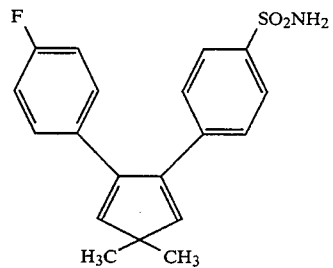

4-[4-(4-Fluorophenyl)-1,1-dimethylcyclopenta-2,4-dien-3-yl]benzenesulfonamide

Step 1: Preparation of 4-[2-(4-fluorophenyl)-4,4-dimethylcyclopenten-1-yl)benzenesulfonamide.

Under nitrogen, a solution of 4.55 g (13.2 mmol) of 1-[2-(4-fluoro phenyl)-4,4-dimethylcyclopenten-1-yl]-4-(methylsulfonyl)benzene (from Step 10 of Example 1) in 50 mL of THF at −78° C. was treated with 6.3 mL (0.27 mmol) of n-butyllithium (2.5 M in hexane) over a period of 5 minutes. The reaction was stirred at ambient temperature for 25 minutes, cooled to −78° C., and treated with 19.8 mL (19.8 mmol) of tributylborane (1.0 M in THF). The resulting dark brown solution was stirred at ambient temperature for 30 minutes and then at reflux for 14 hours prior to the addition of 8.7 g (106 mmol) of sodium acetate, 37 mL of water, and 5.2 g (46 mmol) of hydroxyamine-O-sulfonic acid. The resulting light orange mixture was stirred at ambient temperature for 6 hours and the aqueous phase extracted with ethyl acetate. The combined extracts were washed with water, brine, dried ($MgSO_4$), and concentrated in vacuo. The residue was chromatographed on silica gel to give 2.0 g (40%) of 4-[2-(4-fluorophenyl)-4,4-dimethylcyclopenten-1yl)benzenesulfonamide as a colorless solid: mp 117°–118° C.; NMR ($CDCl_3$) §1.24 (s, 6H), 2.70 (s, 4H), 4.72 (s, 2H), 6.92 (t, J=9 Hz, 2H), 7.09 (dd, J=9 and 7 Hz, 2H), 7.26 (d, J=8 Hz, 2H), 7.74 (d, J=9 Hz, 2H). HRMS. Calc'd for $C_{19}H_{20}FNO_2S$: 345.1199. Found: 345.1194. Anal. Calc'd for [$C_{19}H_{20}FNO_2S$+0.27 $H_2O$]:

C, 65.14; H, 5.91; N, 4.00; S, 9.11. Found: C, 65.07; H, 5.94; N, 3.86; S, 9.29.

Step 2: Preparation of 4-[4-(4-fluorophenyl)-1,1-dimethylcyclopenta-2,4-dien-3-yl]benzenesulfonamide, A solution of 1.0 g (2.89 mmol) of 4-[2-(4-fluorophenyl)-4,4-dimethylcyclopenten-1yl)benzenesulfonamide (from Step 2) in 20 mL of dichloromethane was treated with 800 mg (80% peroxyacid, 3.7 mmol) of m-chloroperoxybenzoic acid (MCPBA). The reaction was stirred at ambient temperature for 3 hours, washed with aqueous saturated sodium bisulfite, dried (MgSO$_4$), and concentrated in vacuo to give a mixture of desired epoxide intermediate and m-chlorobenzoic acid; this crude mixture in 15 mL of acetic acid and 2 mL of water was subsequently treated with 1.0 g (12.2 mmol) of sodium acetate and stirred at 80° C. for 15 hours. The reaction mixture was cooled to ambient temperature and concentrated in vacuo. The residue was partitioned between water and ethyl acetate; the organic phase was washed with aqueous saturated sodiun bicarbonate, water, brine, dried (MgSO$_4$), and reconcentrated in vacuo. Purification by silica gel chromatography gave 665 mg (67%) of 4-[4-(4-fluorophenyl)-1,1-dimethylcyclopenta-2,4-dien-3-yl]benzenesulfonamide as a colorless solid: mp 163.5°–164.5° C. (dec); NMR (CDCl$_3$) d 1.33 (s, 6H), 4.83 (br s, 2H), 6.34 (d, J=2 Hz, 1H), 6.45 (d, J=2 Hz, 1H), 6.94 (t, J=9 Hz, 2H), 7.00–7.20 (m, 2H), 7.25 (d, J=8 Hz, 2H), 7.78 (d, J=8 Hz, 2H).

BIOLOGICAL EVALUATION

Rat Carrageenan Foot Pad Edema Test

The carrageenan foot edema test was performed with materials, reagents and procedures essentially as described by Winter, et al., (*Proc, Soc, Exp. Biol, Med,,* 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs,* in *Nonsteroidal Anti-Inflammatory Drugs,* (J. Lombardino, ed. 1985)). Results are shown in Table I.

Rat Carrageenan-induced Analgesia Test

The analgesia test using rat carrageenan was performed with materials, reagents and procedures essentially as described by Hargreaves, et al., (*Pain,* 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| | RAT PAW EDEMA<br>% Inhibition<br>@ 30 mg/kg body weight | ANALGESIA<br>% Inhibition<br>@30 mg/kg body weight |
|---|---|---|
| Example 1 | 20 | 9 |

Evaluation of COX I and COX II activity in vitro

The compounds of this invention exhibited inhibition in vitro of COX II. The COX II inhibition activity of the compounds of this invention illustrated in the Examples was determined by the following methods.

a. Preparation of recombinant COX baculoviruses

A 2.0 kb fragment containing the coding region of either human or murine COX-I or human or murine COX-II was cloned into a BamH1 site of the baculovirus transfer vector pVL1393 (Invitrogen) to generate the baculovirus transfer vectors for COX-I and COX-II in a manner similar to the method of D. R. O'Reilly et al (Baculovirus Expression Vectors: A Laboratory Manual (1992)). Recombinant baculoviruses were isolated by transfecting 4 µg of baculovirus transfer vector DNA into SF9 insect cells (2×10e8) along with 200 ng of linearized baculovirus plasmid DNA by the calcium phosphate method. See M .D. Summers and G. E. Smith, A Manual of Methods for Baculovirus Vectors and Insect Cell Culture Procdures. Texas Agric. Exp. Station Bull. 1555 (1987). Recombinant viruses were purified by three rounds of plaque purification and high titer (10E7–10E8 pfu/ml) stocks of virus were prepared. For large scale production, SF9 insect cells were infected in 10 liter fermentors (0.5×10$^6$/ml) with the recombinant bacutovirus stock such that the multiplicity of infection was 0.1. After 72 hours the cells were centrifuged and the cell pellet homogenized in Tris/Sucrose (50 mM: 25%, pH 8.0)containing 1% 3-[(3-cholamidopropyl)dimethylammonio]-1-propanesulfonate (CHAPS). The homogenate was centrifuged at 10,000xG for 30 minutes, and the resultant supernatant was stored at −80° C. before being assayed for COX activity.

b. Assay for COX I and COX II activity:

COX activity was assayed as PGE$_2$ formed/µg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 µM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 µl of reaction mix into 160 µl ELISA buffer and 25 µM indomethacin. The PGE$_2$ formed was measured by standard ELISA technology (Cayman Chemical). Results are shown in Table II.

TABLE II

| Example | COX I ID$_{50}$ μM | COX II ID$_{50}$ μM |
|---|---|---|
| 1 | 3.68 | .05 |
| 2 | .02 | <.01 |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 1000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably from about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

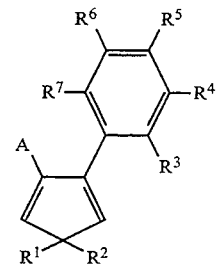

wherein A is selected from

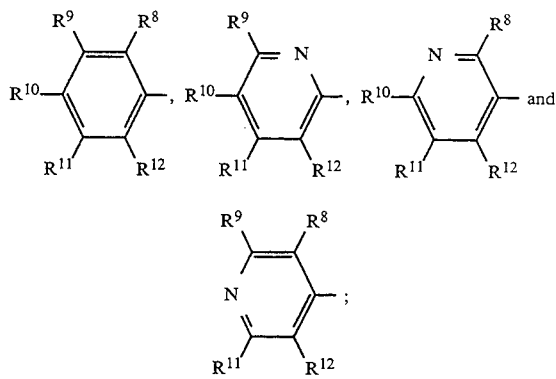

wherein each of $R^1$ and $R^2$ is independently selected from alkyl, hydrido, hydroxyalkyl, halo, haloalkyl, alkoxycarbonyl and carboxyl; and wherein each of $R^3$ through $R^{12}$ is independently selected from hydrido, halo, alkyl, alkylthio, cyano, hydroxyl, mercapto, haloalkyl, alkoxy, haloalkoxy, hydroxyalkyl, alkoxyalkyl, alkylsulfonyl, haloalkylsulfonyl and sulfamyl;

provided that when A is

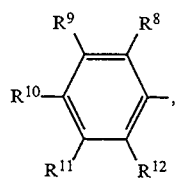

$R^5$ and $R^{10}$ are not both hydrido or methoxy; or a pharmaceutically suitable salt or prodrug thereof.

2. Compound of claim 1 wherein each of $R^1$ and $R^2$ is independently selected from hydrido, lower alkyl, lower hydroxyalkyl, halo, lower haloalkyl, lower alkoxycarbonyl and carboxyl; and wherein each of R³ through R¹² is independently selected from hydrido, halo, lower alkyl, lower alkylthio, cyano, hydroxyl, mercapto, lower haloalkyl, lower haloalkoxy, lower alkoxy, lower hydroxyalkyl, lower alkoxyalkyl, lower alkylsulfonyl, lower haloalkylsulfonyl and sulfamyl; or a pharmaceutically suitable salt or prodrug thereof.

3. Compound of claim 2 wherein each of R¹ and R² is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of R³ through R¹² is independently selected from hydrido, fluoro, chloro, bromo, iodo, methyl, ethyl, propyl, butyl, pentyl, isopropyl, isobutyl, tertbutyl, pentyl, hexyl, methylthio, cyano, hydroxyl, mercapto, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, trifluoromethylsulfonyl and sulfamyl; or a pharmaceutically suitable salt or prodrug thereof.

4. A compound of Formula II

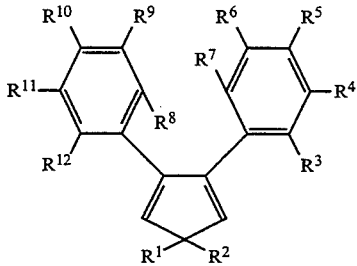

II wherein each of R¹ and R² is independently selected from alkyl, hydrido, hydroxyalkyl, halo, haloalkyl, alkoxycarbonyl and carboxyl; and wherein each of R³ through R¹² is independently selected from hydrido, halo, alkyl, alkylthio, cyano, hydroxyl, mercapto, haloalkyl, alkoxy, haloalkoxy, hydroxyalkyl, alkoxyalkyl, alkylsulfonyl, haloalkylsulfonyl and sulfamyl;

provided R⁵ and R¹⁰ are not both hydrido or methoxy; or a pharmaceutically suitable salt or prodrug thereof.

5. Compound of claim 4 wherein each of R¹ and R² is independently selected from hydrido, lower alkyl, lower hydroxyalkyl, halo, lower haloalkyl, lower alkoxycarbonyl and carboxyl; and wherein each of R³ through R¹² is independently selected from hydrido, halo, lower alkyl, lower alkylthio, cyano, hydroxyl, mercapto, lower haloalkyl, lower haloalkoxy, lower alkoxy, lower hydroxyalkyl, lower alkoxyalkyl, lower alkylsulfonyl, lower haloalkylsulfonyl and sulfamyl; or a pharmaceutically suitable salt or prodrug thereof.

6. Compound of claim 5 wherein each of R¹ and R² is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of R³ through R¹² is independently selected from hydrido, fluoro, chloro, bromo, iodo, methyl, ethyl, propyl, butyl, pentyl, isopropyl, isobutyl, tert-butyl, pentyl, hexyl, methylthio, cyano, hydroxyl, mercapto, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, trifluoromethylsulfonyl and sulfamyl; or a pharmaceutically suitable salt or prodrug thereof.

7. Compound of claim 6 selected from compounds, their prodrugs and their pharmaceutically-acceptable salts, of the group consisting of 1-methylsulfonyl-4-[4-(4-fluorophenyl)cyclopenta-2,4-dien-3-yl]benzene;

1-methylsulfonyl-4-[4-(4-chlorophenyl)cyclopenta-2,4-dien-3-yl]benzene;

1-methylsulfonyl-4-[4-(4-methylphenyl)cyclopenta-2,4-dien-3-yl]benzene;

1-methylsulfonyl-4-[4-(4-trifluoromethylphenyl)cyclopenta-2,4-dien-3-yl]benzene;

1-methylsulfonyl-4-[4-(3-methyl-4-methoxyphenyl)cyclopenta-2,4-dien-3-yl]benzene;

1-methylsulfonyl-4-[4-(3-fluoro-4-methoxyphenyl)cyclopenta-2,4-dien-3-yl]benzene;

1-methylsulfonyl-4-[4-(3-chloro-4-methoxyphenyl)cyclopenta-2,4-dien-3-yl]benzene;

1-methylsulfonyl-4-[4-(3-trifluoromethyl-4-methoxyphenyl)cyclopenta-2,4-dien-3-yl]benzene;

1-methylsulfonyl-4-[4-(3-methyl-4-trifluoromethylphenyl)cyclopenta-2,4-dien-3-yl]benzene;

1-methylsulfonyl-4-[4-(3-fluoro-4-trifluoromethylphenyl)cyclopenta-2,4-dien-3-yl]benzene;

1-methylsulfonyl-4-[4-(3-chloro-4-trifluoromethylphenyl)cyclopenta-2,4-dien-3-yl]benzene;

1-methylsulfonyl-4-[4-(3,4-bis(trifluoromethyl)phenyl)-cyclopenta-2,4-dien-3-yl]benzene;

4-[4-(4-fluorophenyl)cyclopenta-2,4-dien-3-yl]benzenesulfonamide;

4-[4-(4-chlorophenyl)cyclopenta-2,4-dien-3-yl]benzenesulfonamide;

4-[4-(4-methylphenyl)cyclopenta-2,4-dien-3-yl]benzenesulfonamide;

4-[4-(4-trifluoromethylphenyl)cyclopenta-2,4-dien-3-yl]benzenesulfonamide;

4-[4-(3-methyl-4-methoxyphenyl)cyclopenta-2,4-dien-3-yl]benzenesulfonamide;

4-[4-(3-fluoro-4-methoxyphenyl)cyclopenta-2,4-dien-3-yl]benzenesulfonamide;

4-[4-(3-chloro-4-methoxyphenyl)cyclopenta-2,4-dien-3-yl]benzenesulfonamide;

4-[4-(3-trifluoromethyl-4-methoxyphenyl)cyclopenta-2,4-dien-3-yl]benzenesulfonamide;

4-[4-(3-methyl-4-trifluoromethylphenyl)cyclopenta-2,4-dien-3-yl]benzenesulfonamide;

4-[4-(3-fluoro-4-trifluoromethylphenyl)cyclopenta-2,4-dien-3-yl]benzenesulfonamide;

4-[4-(3-chloro-4-trifluoromethylphenyl)cyclopenta-2,4-dien-3-yl]benzenesulfonamide;

4-[4-(3,4-bis(trifluoromethyl)phenyl)cyclopenta-2,4-dien-3-yl]benzenesulfonamide;

1-methylsulfonyl-4-[4-(4-fluorophenyl)-1,1-dimethylcyclopenta-2,4-dien-3-yl]benzene;

1-methylsulfonyl-4-[4-(4-fluorophenyl)-1,1-diethylcyclopenta-2,4-dien-3-yl]benzene;

1-methylsulfonyl -4-[4-(4-fluorophenyl)-1,1-difluorocyclopenta-2,4-dien-3-yl]benzene;

1-methylsulfonyl-4-[4-(4-fluorophenyl)-1,1-bis(trifluoromethyl)cyclopenta-2,4-dien-3-yl]benzene;

1-methylsulfonyl-4-[4-(4-trifluoromethylphenyl)-1,1-dimethylcyclopenta-2,4-dien-3-yl]benzene;

1-methylsulfonyl-4-[4-(4-trifluoromethylphenyl)-1,1-difluorocyclopenta-2,4-dien-3-yl]benzene;

1-methylsulfonyl -4-[4-(4-trifluoromethylphenyl)-1,1-bis(trifluoromethyl)cyclopenta-2,4-dien-3-yl]benzene;

4-[4-(4-fluorophenyl)-1,1-dimethylcyclopenta-2,4-diene-3-yl]benzenesulfonamide;

4-[4-(4-fluorophenyl)-1,1-difluorocyclopenta-2,4-diene-3-yl]benzenesulfonamide;

4-[4-(4-fluorophenyl)-1,1-bis(trifluoromethyl)cyclopenta-2,4-diene-3-yl]benzenesulfonamide;

4-[4-(4-trifluoromethylphenyl)-1,1-dimethylcyclopenta-2,4-diene-3-yl]benzenesulfonamide;

4-[4-(4-trifluoromethylphenyl)-1,1-difluorocyclopenta-2,4-diene-3-yl]benzenesulfonamide;

4-[4-(4-trifluoromethylphenyl)-1,1-bis(trifluoromethyl)cyclopenta-2,4-diene-3-yl]benzenesulfonamide;

1-methylsulfonyl-4-[4-(4-fluorophenyl)-1-trifluoromethylcyclopenta-2,4-dien-3-yl]benzene;

1-methylsulfonyl-4-[4-(4-trifluoromethylphenyl)-1-trifluoromethylcyclopenta-2,4-dien-3-yl]benzene;

4-[4-(4-fluorophenyl)-1-trifluoromethylcyclopenta-2,4-dien-3-yl]benzenesulfonamide; and 4-[4-(4-trifluoromethylphenyl)-1-trifluoromethylcyclopenta-2,4-dien-3-yl]benzenesulfonamide.

8. Compound of claim 6 which is 1-methylsulfonyl-4-[1,1-dimethyl-4-(4-fluorophenyl)cyclopenta-2,4-dien-3-yl]benzene, or a pharmaceutically-acceptable salt or prodrug thereof.

9. Compound of claim 6 which is 4-[4-(4-fluorophenyl)-1,1-dimethylcyclopenta-2,4-dien-3yl]benzenesulfonamide, or a pharmaceutically-acceptable salt or prodrug thereof.

10. A compound of Formula III

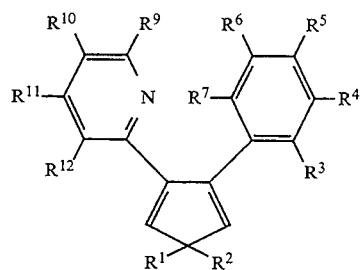

wherein each of $R^1$ and $R^2$ is independently selected from hydrido, alkyl, hydroxyalkyl, halo, haloalkyl, alkoxycarbonyl and carboxyl; and wherein each of $R^3$ through $R^7$ and $R^9$ through $R^{12}$ is independently selected from hydrido, halo, alkyl, alkylthio, cyano, hydroxyl, mercapto, haloalkyl, alkoxy, haloalkoxy, hydroxyalkyl, alkoxyalkyl, alkylsulfonyl, haloalkylsulfonyl and sulfamyl; or a pharmaceutically-acceptable salt thereof.

11. Compound of claim 10 wherein each of $R^1$ and $R^2$ is independently selected from hydrido, lower alkyl, lower hydroxyalkyl, halo, lower haloalkyl, lower alkoxycarbonyl and carboxyl; and wherein each of $R^3$ through $R^7$ and $R^9$ through $R^{12}$ is independently selected from hydrido, halo, lower alkyl, lower alkylthio, cyano, hydroxyl, mercapto, lower haloalkyl, lower haloalkoxy, lower alkoxy, lower hydroxyalkyl, lower alkoxyalkyl, lower alkylsulfonyl, lower haloalkylsulfonyl and sulfamyl; or a pharmaceutically suitable salt or prodrug thereof.

12. Compound of claim 11 wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^7$ and $R^9$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, hydroxyl, mercapto, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, trifluoromethylsulfonyl and sulfamyl; or a pharmaceutically-acceptable salt or prodrug thereof.

13. Compound of claim 12 selected from compounds, their prodrugs and their pharmaceutically-acceptable salts, of the group consisting of 5-fluoro-2-[4-[4-(methylsulfonyl)phenyl]cyclopenta-2,4-dien-3-yl]pyridine;

5-chloro-2-[4-[4-(methylsulfonyl)phenyl]cyclopenta-2,4-dien-3-yl]pyridine;

5-methyl-2-[4-[4-(methyl sulfonyl)phenyl]cyclopenta-2,4-dien-3-yl]pyridine;

5-trifluoromethyl-2-[4-[4-(methylsulfonyl) phenyl]cyclopenta-2,4-dien-3-yl]pyridine;

4-[4-(5-fluoropyrid-2-yl)cyclopenta-2,4-dien-3-yl]benzenesulfonamide;

4-[4-(5-chloropyrid-2-yl)cyclopenta-2,4-dien-3-yl]benzenesulfonamide;

4-[4-(5-methylpyrid-2-yl)cyclopenta-2,4-dien-3-yl]benzenesulfonamide;

4-[4-(5-trifluoromethylpyrid-2-yl)cyclopenta-2,4-dien-3-yl]benzenesulfonamide;

5-fluoro-2-[4-[4-(methylsulfonyl)phenyl]-1-trifluoromethylcyclopenta-2,4-dien-3-yl]pyridine;

5-trifluoromethyl-2-[4-[4-(methylsulfonyl)phenyl]-1-trifluoromethylcyclopenta-2,4-dien-3-yl]pyridine;

4-[4-(5-fluoropyrid-2-yl)-1-trifluoromethylcyclopenta-2,4-dien-3-yl]benzenesulfonamide;

4-[4-(5-trifluoromethylpyrid-2-yl)-1-trifluoromethylcyclopenta-2,4-dien-3-yl]benzenesulfonamide;

5-fluoro-2-[4-[4-(methylsulfonyl)phenyl]-1,1-dimethylcyclopenta-2,4-dien-3-yl]pyridine;

5-fluoro-2-[4-[4-(methylsulfonyl)phenyl]-1,1-bis(trifluoromethyl)cyclopenta-2,4-dien-3-yl]pyridine;

5-trifluoromethyl-2-[4-[4-(methylsulfonyl)phenyl]-1,1-dimethylcyclopenta-2,4-dien-3-yl]pyridine;

5-trifluoromethyl-2-[4-[4-(methylsulfonyl)phenyl]-1,1bis(trifluoromethyl)cyclopenta-2,4-dien-3yl]pyridine;

4-[2-(5-fluoropyrid-2-yl)-4,4-dimethylcyclopenta-2,4-dien-3-yl]benzenesulfonamide;

4-[2-(5-fluoropyrid-2-yl)-4,4-bis(trifluoromethyl)cyclopenta-2,4-dien-3-yl]benzenesulfonamide;

4-[2-(5-trifluoromethylpyrid-2-yl)-4,4-dimethylcyclopenta-2,4-dien-3-yl]benzenesulfonamide;

4-[2-(5-trifluoromethylpyrid-2-yl)-4,4-bis(trifluoromethyl)cyclopenta-2,4-dien-3-yl]benzenesulfonamide;

2-[4-(4-fluorophenyl)cyclopenta-2,4-dien-3-yl]-5-(methylsulfonyl)pyridine;

2-[4-(4-chlorophenyl)cyclopenta-2,4-dien-3-yl]-5-(methylsulfonyl)pyridine;

2-[4-(4-methylphenyl)cyclopenta-2,4-dien-3-yl]-5-(methylsulfonyl)pyridine;

2-[4-(4-trifluoromethylphenyl)cyclopenta-2,4-dien-3-yl]-5-(methylsulfonyl)pyridine;

2-[4-(4-fluorophenyl)cyclopenta-2,4-dien-3-yl]-5-pyridinesulfonamide;

2-[4-(4-chlorophenyl)cyclopenta-2,4-dien-3-yl]-5-pyridinesulfonamide;

2-[4-(4-methylphenyl)cyclopenta-2,4-dien-3-yl]-5-pyridinesulfonamide;

2-[4-(4-trifluoromethylphenyl)cyclopenta-2,4-dien-3-yl]-5-pyridinesulfonamide;

2-[4-(4-fluorophenyl)-1-trifluoromethylcyclopentena-2,4-dien-3-yl]-5-(methylsulfonyl)pyridine;

2-[4-(4-trifluoromethylphenyl)-1-(trifluoromethyl)cyclopentena-2,4-dien-3-yl]-5-(methylsulfonyl)pyridine;

2-[4-(4-fluorophenyl)-1-trifluoromethylcyclopenta-2,4-dien-3-yl]-5-pyridinesulfonamide;

2-[4-(4-trifluoromethylphenyl)-1-(trifluoromethyl)cyclopenta-2,4-dien-3-yl]-5-pyridinesulfonamide;

2-[4-(4-fluorophenyl)-1,1-dimethylcyclopenta-2,4-dien-3-yl]-5-(methylsulfonyl)pyridine;

2-[4-(4-fluorophenyl)-1,1-bis(trifluoromethyl)cyclopenta-2,4-dien-3-yl]-5-(methylsulfonyl)pyridine;

2-[4- {4-trifluoromethylphenyl)-1,1-dimethylcyclopenta-2,4-dien-3-yl]-5-(methylsulfonyl)pyridine;

2-[4-(4-trifluoromethylphenyl)-1,1-bis(trifluoromethyl)cyclopenta-2,4-dien-3-yl]-5-(methylsulfonyl)pyridine;

2-[4-(4-fluorophenyl)-1,1-dimethylcyclopenta-2,4-dien-3-yl]-5-pyridinesulfonamide;

2-[4-(4-fluorophenyl)-1,1-bis(trifluoromethyl)cyclopenta-2,4-dien-3-yl]-5-pyridinesulfonamide;

2-[4-(4-trifluoromethylphenyl)-1,1-dimethylcyclopenta-2,4-dien-3-yl]-5-pyridinesulfonamide; and 2-[4-(4-trifluoromethylphenyl)-1,1-bis(trifluoromethyl)cyclopenta-2,4-dien-3-yl]-5-pyridinesulfonamide.

14. A compound of Formula IV

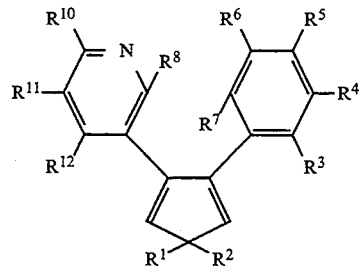

wherein each of $R^1$ and $R^2$ is independently selected from hydrido, alkyl, hydroxyalkyl, halo, haloalkyl, alkoxycarbonyl and carboxyl; and wherein each of $R^3$ through $R^8$ and $R^{10}$ through $R^{12}$ is independently selected from hydrido, halo, alkyl, alkylthio, cyano, hydroxyl, mercapto, haloalkyl, alkoxy, haloalkoxy, hydroxyalkyl, alkoxyalkyl, alkylsulfonyl, haloalkylsulfonyl and sulfamyl;

or a pharmaceutically-acceptable salt or prodrug thereof.

15. The compound of claim 14 wherein each of $R^1$ and $R^2$ is independently selected from hydrido, lower alkyl, lower hydroxyalkyl, halo, lower haloalkyl, lower alkoxycarbonyl and carboxyl; and wherein each of $R^3$ through $R^8$ and $R^{10}$ through $R^{12}$ is independently selected from hydrido, halo, lower alkyl, lower alkylthio, cyano, hydroxyl, mercapto, lower haloalkyl, lower haloalkoxy, lower alkoxy, lower hydroxyalkyl, lower alkoxyalkyl, lower alkylsulfonyl, lower haloalkylsulfonyl and sulfamyl; or a pharmaceutically suitable salt or prodrug thereof.

16. Compound of claim 15 wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^8$ and $R^{10}$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, hydroxyl, mercapto, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tertbutoxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, trifluoromethylsulfonyl and sulfamyl; or a pharmaceutically-acceptable salt or prodrug thereof.

17. Compound of claim 16 selected from compounds, their prodrugs and their pharmaceutically-acceptable salts, of the group consisting of 2-fluoro -5-[4-[4-(methylsulfonyl)phenyl]cyclopenta-2,4-dien-3-yl]pyridine;

2-chloro-5-[4-[4-(methylsulfonyl)phenyl]cyclopenta-2,4-dien-3-yl]pyridine;

2-methyl-5-[4-[4-(methylsulfonyl)phenyl]cyclopenta-2,4-dien-3-yl]pyridine;

2-trifluoromethyl-5-[4-[4-(methylsulfonyl)phenyl]cyclopenta-2,4-dien-3-yl]pyridine;

4-[4-(2-fluoropyrid-5-yl)cyclopenta-2,4-dien-3-yl]benzenesulfonamide;

4-[4-(2-chloropyrid-5-yl)cyclopenta-2,4-dien-3-yl]benzenesulfonamide;

4-[4-(2-methylpyrid-5-yl)cyclopenta-2,4-dien-3-yl]benzenesulfonamide;

4-[4-(2-trifluoromethylpyrid-5-yl)cyclopenta-2,4-alien-3-yl]benzenesulfonamide;

2-fluoro-5-[4-[4-(methylsulfonyl)phenyl]-1-trifluormethylcyclopenta-2,4-dien-3-yl]pyridine 2-trifluoromethyl-5-[4-[4-(methylsulfonyl)phenyl]-1-trifluormethylcyclopenta-2,4-dien-3-yl]pyridine 4-[2-(2-fluoropyrid-5-yl)-1-trifluoromethylcyclopenta-2,4-dien-3-yl]benzenesulfonamide;

4-[2-(2-trifluoromethylpyrid-5-yl)-1-trifluoromethylcyclopenta-2,4-dien-3-yl]benzenesulfonamide;

2-fluoro-5-[4-[4-(methylsulfonyl)phenyl]-1,1-dimethylcyclopenta-2,4-dien-3-yl]pyridine;

2-fluoro-5-[4-[4-(methylsulfonyl)phenyl]-1,1-bis(trifluoromethyl)cyclopenta-2,4-dien-3-yl]pyridine;

2-trifluoromethyl-5-[4-[4-(methylsulfonyl)phenyl]-1,1-dimethylcyclopenta-2,4-dien-3-yl]pyridine;

2-trifluoromethyl-5-[4-[4-(methylsulfonyl)phenyl]-1,1-bis(trifluoromethyl)cyclopenta-2,4-dien-3-yl]pyridine;

4-[4-(2-fluoropyrid-5-yl)-1,1-dimethylcyclopenta-2,4-dien-3-yl]benzenesulfonamide;

4-[4-(2-fluoropyrid-5-yl)-1,1-bis(trifluoromethyl)cyclopenta-2,4-dien-3-yl]benzenesulfonamide;

4-[4-(2-trifluoromethylpyrid-5-yl)-1,1-dimethylcyclopenta-2,4-dien-3-yl]benzenesulfonamide;

4-[4-(2-trifluoromethylpyrid-5-yl)-1,1-bis(trifluoromethyl)cyclopenta-2,4-dien-3-yl]benzenesulfonamide;

5-[4-(4-fluorophenyl)cyclopenta-2,4-dien-3-yl]-2-(methylsulfonyl)pyridine;

5-[4-(4-chlorophenyl)cyclopenta-2,4-dien-3-yl]-2-(methylsulfonyl)pyridine;

5-[4-(4-methylphenyl)cyclopenta-2,4-dien-3-yl]-2-(methylsulfonyl)pyridine;

5-[4-(4-trifluoromethylphenyl)cyclopenta-2,4-dien-3-yl]--(methylsulfonyl)pyridine;

5-[4-(4-fluorophenyl)cyclopenta-2,4-dien-3-yl]-2-pyridinesulfonamide;

5-[4-(4-chlorophenyl)cyclopenta-2,4-dien-3-yl]-2-pyridinesulfonamide;

5-[4-(4-methylphenyl)cyclopenta-2,4-dien-3-yl]-2-pyridinesulfonamide;

5-[4-(4-trifluoromethylphenyl)cyclopenta-2,4-dien-3-yl]-2-pyridinesulfonamide;

5-[4-(4-fluorophenyl)-1-(trifluoromethyl)cyclopenta-2,4-dien-3-yl]-2-(methylsulfonyl)pyridine;

5-[4-(4-trifluoromethylphenyl)-1-(trifluoromethyl)cyclopenta-2,4-dien-3-yl]-2-(methylsulfonyl)pyridine;

5-[4-(4-fluorophenyl)-1-trifluoromethylcyclopenta-2,4-dien-3-yl]-2-pyridinesulfonamide;

5-[4-(4-trifluoromethylphenyl)-1-trifluoromethylcyclopenta-2,4-dien-3-yl]-2-pyridinesulfonamide;

5-[4-(4-fluorophenyl)-1,1-dimethylcyclopenta-2,4-dien-3-yl]-2-(methylsulfonyl)pyridine;

5-[4-(4-fluorophenyl)-1,1-bis(trifluoromethyl)cyclopenta-2,4-dien-3-yl]-2-(methylsulfonyl)pyridine;

5-[4-(4-trifluoromethylphenyl)-1,1-dimethylcyclopenta-2,4-dien-3-yl]-2-(methylsulfonyl)pyridine;

5-[4-(4-trifluoromethylphenyl)-1,1-bis(trifluoromethyl)-cyclopenta-2,4-dien-3-yl]-2 (methylsulfonyl)pyridine;

5-[4-(4-fluorophenyl)-1,1-dimethylcyclopenta-2,4-dien-3-yl]-2-pyridinesulfonamide;

5-[4-(4-fluorophenyl)-1,1-bis(trifluoromethyl)cyclopenta-2,4-dien-3-yl]-2-pyridinesulfonamide;

5-[4-(4-trifluoromethylphenyl)-1,1-dimethylcyclopenta-2,4-dien-3-yl]-2-pyridinesulfonamide;

5-[4-(4-trifluoromethylphenyl)-1,1-bis(trifluoromethyl)-cyclopenta-2,4-dien-3-yl]-2-(methylsulfonyl)pyridine;

1-methylsulfonyl-4-[1-methyl-1-trifluoromethyl-4-(4-fluorophenyl)cyclopenta-2,4-dien-3-yl]benzene; and 1-methylsulfonyl-4-[1-methyl-1-trifluoromethyl-4-(4-chlorophenyl)cyclopenta-2,4-dien-3-yl]benzene.

18. A compound of Formula V

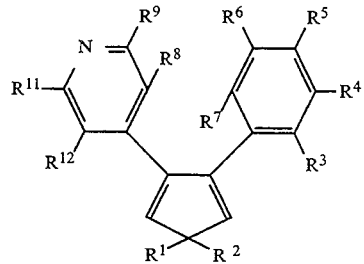

wherein each of $R^1$ and $R^2$ is independently selected from hydrido, alkyl, hydroxyalkyl, halo, haloalkyl, alkoxycarbonyl and carboxyl; and wherein each of $R^3$ through $R^9$, $R^{11}$ and $R^{12}$ is independently selected from hydrido, halo, alkyl, alkylthio, cyano, hydroxyl, mercapto, haloalkyl, alkoxy, haloalkoxy, hydroxyalkyl, alkoxyalkyl, alkylsulfonyl, haloalkylsulfonyl and sulfamyl;

or a pharmaceutically-acceptable salt or prodrug thereof or a pharmaceutically-acceptable salt or prodrug thereof.

19. The compound of claim 18 wherein each of $R^1$ and $R^2$ is independently selected from hydrido, lower alkyl, lower hydroxyalkyl, halo, lower haloalkyl, lower alkoxycarbonyl and carboxyl; and wherein each of $R^3$ through $R^9$, $R^{11}$ and $R^{12}$ is independently selected from hydrido, halo, lower alkyl, lower alkylthio, cyano, hydroxyl, mercapto, lower haloalkyl, lower alkoxy, lower haloalkoxy, lower hydroxyalkyl, lower alkoxyalkyl, lower alkylsulfonyl, lower haloalkylsulfonyl and sulfamyl; or a pharmaceutically suitable salt or prodrug thereof.

20. Compound of claim 19 wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^9$, $R^{11}$ and $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, hydroxyl, mercapto, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, trifluoromethylsulfonyl and sulfamyl; or a pharmaceutically-acceptable salt or prodrug thereof.

21. Compound of claim 20 selected from compounds, their prodrugs and their pharmaceutically-acceptable salts, of the group consisting of 4-[4-[4-(methylsulfonyl)phenyl]cyclopenta-2,4-dien-3-yl]pyridine;

4-[4-(4-pyridyl)cyclopenta-2,4-dien-3-yl]benzenesulfonamide;

4-[4-[4-(methylsulfonyl)phenyl]-1,1-dimethylcyclopenta-2,4-dien-3-yl]pyridine;

4-[4-[4-(methylsulfonyl)phenyl]-1,1-di(hydroxymethyl)-cyclopenta-2,4-dien-3-yl]pyridine;

4-[4-[4-(methylsulfonyl)phenyl]-1,1-di fluorocyclopenta-2,4-dien-3-yl]pyridine;

4-[4-[4-(methylsulfonyl)phenyl]-1,1-di(fluoromethyl)-cyclopenta-2,4-dien-3-yl]pyridine;

4-[4-(4-pyridyl)-1,1-dimethylcyclopenta-2,4-dien-3-yl]benzenesulfonamide;

4-[4-(4-pyridyl)-1,1-difluorocyclopenta-2,4-dien-3-yl]benzenesulfonamide;

4-[4-(4-pyridyl)-1,1-di (fluoromethyl)cyclopenta-2,4-dien-3-yl]benzenesulfonamide; and 4-[4-(4-pyridyl)-1,1-bis(trifluoromethyl)cyclopenta-2,4-dien-3-yl]benzenesulfonamide.

22. A pharmaceutical composition comprising a therapeutically-effective amount of a compound, said compound selected from a family of compounds of claim 4; or a pharmaceutically-acceptable salt or prodrug thereof.

23. A pharmaceutical composition comprising a therapeutically-effective amount of a compound, said compound selected from a family of compounds of claim 5; or a pharmaceutically-acceptable salt or prodrug thereof.

24. A pharmaceutical composition comprising a therapeutically-effective amount of a compound, said compound selected from a family of compounds of claim 6; or a pharmaceutically-acceptable salt or prodrug thereof.

25. A pharmaceutical composition comprising a therapeutically-effective amount of a compound, said compound selected from a family of compounds of claim 7; or a pharmaceutically-acceptable salt or prodrug thereof.

26. A pharmaceutical composition comprising a therapeutically-effective amount of a compound, said compound selected from a compound of claim 8; or a pharmaceutically-acceptable salt or prodrug thereof.

27. A pharmaceutical composition comprising a therapeutically-effective amount of a compound, said compound selected from a compound of claim 9; or a pharmaceutically-acceptable salt or prodrug thereof.

28. A method of treating inflammation or an inflammation-associated disorder in a subject, said method comprising administering to the subject having such inflammation or inflammation-associated disorder, a therapeutically-effective amount of a compound of claim 4; or a pharmaceutically-acceptable salt or prodrug thereof.

29. A method of treating inflammation or an inflammation-associated disorder in a subject, said method comprising administering to the subject having such inflammation or inflammation-associated disorder, a therapeutically-effective amount of a compound of claim 5; or a pharmaceutically-acceptable salt or prodrug thereof.

30. A method of treating inflammation or an inflammation-associated disorder in a subject, said method comprising administering to the subject having such inflammation or inflammation-associated disorder, a therapeutically-effective amount of a compound of claim 6; or a pharmaceutically-acceptable salt or prodrug thereof.

31. A method of treating inflammation or an inflammation-associated disorder in a subject, said method comprising administering to the subject having such inflammation or inflammation-associated disorder, a therapeutically-effective amount of a compound of claim 7; or a pharmaceutically-acceptable salt or prodrug thereof.

32. A method of treating inflammation or an inflammation-associated disorder in a subject, said method comprising administering to the subject having such inflammation or inflammation-associated disorder, a therapeutically-effective amount of a compound of claim 8; or a pharmaceutically-acceptable salt or prodrug thereof.

33. A method of treating inflammation or an inflammation-associated disorder in a subject, said method comprising administering to the subject having such inflammation or inflammation-associated disorder, a therapeutically-effective amount of a compound of claim 9; or a pharmaceutically-acceptable salt or prodrug thereof.

34. The method of claim 28 for use in treatment of inflammation.

35. The method of claim 28 for use in treatment of an inflammation-associated disorder.

36. The method of claim 35 wherein the inflammation-associated disorder is arthritis.

37. The method of claim 35 wherein the inflammation-associated disorder is pain.

38. The method of claim 35 wherein the inflammation-associated disorder is fever.

* * * * *